US007645733B2

(12) United States Patent
Brines et al.

(10) Patent No.: US 7,645,733 B2
(45) Date of Patent: Jan. 12, 2010

(54) TISSUE PROTECTIVE CYTOKINES FOR THE TREATMENT AND PREVENTION OF SEPSIS AND THE FORMATION OF ADHESIONS

(75) Inventors: Michael Brines, Woodbridge, CT (US); Anthony Cerami, Somers, NY (US); Thomas Coleman, Mt. Kisco, NY (US); Osman Yilmaz, Gottepe (TR)

(73) Assignees: The Kenneth S. Warren Institute, Inc., Ossining, NY (US); Warren Pharmaceuticals, Inc., Ossinin, NY (US)

( * ) Notice: Subject to any disclaimer, the term of this patent is extended or adjusted under 35 U.S.C. 154(b) by 251 days.

(21) Appl. No.: 10/573,905

(22) PCT Filed: Sep. 29, 2004

(86) PCT No.: PCT/US2004/031789

§ 371 (c)(1), (2), (4) Date: May 30, 2006

(87) PCT Pub. No.: WO2005/032467

PCT Pub. Date: Apr. 14, 2005

(65) Prior Publication Data

US 2007/0129293 A1 Jun. 7, 2007

Related U.S. Application Data

(60) Provisional application No. 60/506,149, filed on Sep. 29, 2003.

(51) Int. Cl.

| | |
|---|---|
| ***A61K 38/18*** | (2006.01) |
| ***A61K 38/22*** | (2006.01) |
| ***C07K 14/505*** | (2006.01) |
| *C07K 1/107* | (2006.01) |

(52) U.S. Cl. .............................. 514/2; 514/8; 530/335; 530/345; 530/397

(58) Field of Classification Search ....................... None
See application file for complete search history.

(56) References Cited

U.S. PATENT DOCUMENTS

| | | | | |
|---|---|---|---|---|
| 4,343,782 | A | 8/1982 | Shapiro | |
| 4,377,513 | A | 3/1983 | Sugimoto et al. | |
| 4,658,019 | A | 4/1987 | Kung et al. | |
| 4,703,008 | A | 10/1987 | Lin | |
| 4,806,524 | A | 2/1989 | Kawaguchi et al. | |
| 4,835,260 | A | 5/1989 | Shoemaker | |
| 4,992,419 | A | 2/1991 | Woog et al. | |
| 5,194,596 | A | 3/1993 | Tischer et al. | |
| 5,278,065 | A | 1/1994 | D'Andrea | |
| 5,292,654 | A | 3/1994 | Yoshimura | |
| 5,350,836 | A | 9/1994 | Kopchick et al. | |
| 5,457,089 | A | 10/1995 | Fibi et al. | |
| 5,547,933 | A | 8/1996 | Lin | |
| 5,571,787 | A | 11/1996 | O'Brien et al. | |
| 5,604,198 | A | 2/1997 | Poduslo et al. | |
| 5,614,184 | A | 3/1997 | Sytkowski et al. | |
| 5,618,698 | A | 4/1997 | Lin | |
| 5,621,080 | A | 4/1997 | Lin | |
| 5,625,035 | A | 4/1997 | Clemons | |
| 5,661,125 | A | 8/1997 | Strickland | |
| 5,696,080 | A | 12/1997 | O' Brien | |
| 5,700,909 | A | 12/1997 | O'Brien | |
| 5,714,459 | A | 2/1998 | O'Brien | |
| 5,750,376 | A | 5/1998 | Weiss et al. | |
| 5,756,349 | A | 5/1998 | Lin | |
| 5,763,198 | A | 6/1998 | Hirth et al. | |
| 5,767,078 | A | 6/1998 | Johnson et al. | |
| 5,773,569 | A | 6/1998 | Wrighton et al. | |
| 5,824,672 | A | 10/1998 | Simpkins et al. | |
| 5,830,851 | A | 11/1998 | Wrighton et al. | |
| 5,835,382 | A | 11/1998 | Wilson et al. | |
| 5,856,298 | A | 1/1999 | Strickland | |
| 5,888,772 | A | 3/1999 | Okasinski et al. | |
| 5,955,422 | A | 9/1999 | Lin | |
| 5,997,865 | A | 12/1999 | Bennett et al. | |
| 6,048,971 | A | 4/2000 | Sytkowski et al. | |
| 6,103,526 | A | 4/2000 | Smith et al. | |
| 6,071,970 | A | 6/2000 | Mueller et al. | |
| 6,153,407 | A | 11/2000 | Sytkowski et al. | |
| 6,165,783 | A | 12/2000 | Weiss et al. | |
| 6,242,570 | B1 | 6/2001 | Sytkowski | |
| 6,291,661 | B1 | 9/2001 | Graddis et al. | |
| 6,340,742 | B1 | 1/2002 | Burg et al. | |
| 6,399,336 | B1 | 6/2002 | Paulson et al. | |
| 6,440,932 | B1 | 8/2002 | Lehmann et al. | |
| 6,489,293 | B1 | 12/2002 | Sytkowski et al. | |
| 6,521,245 | B1 | 2/2003 | Zaharia | |
| 6,531,121 | B2 | 3/2003 | Brines et al. | |
| 6,583,272 | B1 | 6/2003 | Bailon | |
| 6,645,522 | B2 | 11/2003 | Naeff et al. | |
| 7,214,532 | B2 | 5/2007 | Stern et al. | |
| 7,300,916 | B2 * | 11/2007 | Yasuda et al. | 514/2 |
| 7,309,687 | B1 | 12/2007 | Brines et al. | |
| 7,345,019 | B1 | 3/2008 | Brines et al. | |

(Continued)

FOREIGN PATENT DOCUMENTS

| | | |
|---|---|---|
| CA | 2294448 | 12/1998 |

(Continued)

OTHER PUBLICATIONS

Abdelrahman, 2004, "Erythropoietin attenuates the tissue injury associated with hemorrhagic shock an myocardial ischemia," Shock, vol. 22(1), pp. 63-69.

(Continued)

*Primary Examiner*—Christine J Saoud
*Assistant Examiner*—Regina M DeBerry
(74) *Attorney, Agent, or Firm*—Jones Day

(57) ABSTRACT

A method of treating, preventing, delaying the onset, and/or reducing the effects of proinflammatory cytokines in conditions including, but not limited to, sepsis, adhesion formation, wounds, organ failure, chronic disease, general inflammatory conditions resulting from infection, scarring resulting from injury and incisions, and combinations thereof.

4 Claims, 9 Drawing Sheets

U.S. PATENT DOCUMENTS

| | | | |
|---|---|---|---|
| 2002/0031806 | A1 | 3/2002 | Lee |
| 2002/0052309 | A1 | 5/2002 | Anagnostou et al. |
| 2002/0061849 | A1 | 5/2002 | Nielsen et al. |
| 2002/0077294 | A1 | 6/2002 | Kay et al. |
| 2002/0081734 | A1 | 6/2002 | Choi et al. |
| 2002/0086816 | A1 | 7/2002 | Brines et al. |
| 2002/0142370 | A1 | 10/2002 | Paulson et al. |
| 2002/0160460 | A1 | 10/2002 | Paulson et al. |
| 2003/0003529 | A1 | 1/2003 | Bayer |
| 2003/0040037 | A1 | 2/2003 | Bayer |
| 2003/0072737 | A1 | 4/2003 | Brines |
| 2003/0077753 | A1 | 4/2003 | Tischer |
| 2003/0083251 | A1 | 5/2003 | Westfenfelder |
| 2003/0104988 | A1 | 6/2003 | Brines |
| 2003/0113871 | A1 | 6/2003 | Lee et al. |
| 2003/0118547 | A1 | 6/2003 | Vandenberg |
| 2003/0120045 | A1 | 6/2003 | Bailon |
| 2003/0124115 | A1 | 7/2003 | Lee et al. |
| 2003/0134798 | A1 | 7/2003 | Brines et al. |
| 2003/0166566 | A1 | 9/2003 | Kinstler et al. |
| 2004/0009902 | A1 | 1/2004 | Boime |
| 2004/0018978 | A1 | 1/2004 | Campana et al. |
| 2004/0091961 | A1 | 5/2004 | Evans et al. |
| 2004/0096447 | A1 | 5/2004 | Yasuda et al. |
| 2004/0122216 | A1 | 6/2004 | Nielsen et al. |
| 2004/0209812 | A1 | 10/2004 | Farrell et al. |
| 2004/0214236 | A1 | 10/2004 | Brines et al. |
| 2005/0176627 | A1 | 8/2005 | Cerami et al. |
| 2006/0034799 | A1 | 2/2006 | Brines et al. |
| 2006/0216757 | A1 | 9/2006 | Brines et al. |
| 2007/0298031 | A1 | 12/2007 | Brines et al. |
| 2008/0045412 | A1 | 2/2008 | Brines et al. |

FOREIGN PATENT DOCUMENTS

| | | |
|---|---|---|
| DE | 198 57 609 | 6/2000 |
| EP | 555880 | 8/1993 |
| EP | 0640619 | 1/1995 |
| EP | 0668 351 | 8/1995 |
| EP | 1064951 | 1/2001 |
| JP | 05092928 | 4/1993 |
| JP | 5-246885 | 9/1993 |
| WO | WO 85/02610 | 6/1985 |
| WO | WO 86/03520 | 6/1986 |
| WO | WO 90/11354 | 10/1990 |
| WO | WO 91/05867 | 5/1991 |
| WO | WO 91/06667 | 5/1991 |
| WO | WO 91/09955 | 7/1991 |
| WO | WO 92/08493 | 5/1992 |
| WO | WO 93/09222 | 5/1993 |
| WO | WO 93/25221 | 12/1993 |
| WO | WO 94/09257 | 4/1994 |
| WO | WO 94/12650 | 6/1994 |
| WO | WO 94/24160 | 10/1994 |
| WO | WO 95/05465 | 2/1995 |
| WO | WO 95/31560 | 11/1995 |
| WO | WO 96/14081 | 5/1996 |
| WO | WO 97/08307 | 3/1997 |
| WO | WO 97/18318 | 5/1997 |
| WO | WO 97/32895 | 9/1997 |
| WO | WO 98/10650 | 3/1998 |
| WO | WO 98/18926 | 5/1998 |
| WO | WO 98/58660 | 12/1998 |
| WO | WO 99/21966 | 5/1999 |
| WO | WO 00/24893 | 5/2000 |
| WO | WO 00/32772 | 6/2000 |
| WO | WO 00/35475 | 6/2000 |
| WO | WO 00/61164 | 10/2000 |
| WO | WO 01/02017 | 1/2001 |
| WO | WO 01/81405 | 1/2001 |
| WO | WO 01/82952 | 11/2001 |
| WO | WO 01/82953 | 11/2001 |
| WO | WO 01/87329 | 11/2001 |
| WO | WO 02/10743 | 2/2002 |
| WO | WO 02/14356 | 2/2002 |
| WO | WO 02/49673 | 6/2002 |
| WO | WO 02/053580 | 7/2002 |
| WO | WO 03/029291 | 4/2003 |
| WO | WO 2004/003176 | 1/2004 |
| WO | WO 2004/004656 | 1/2004 |
| WO | WO 2004/022577 | 3/2004 |
| WO | WO 2004/096148 | 11/2004 |
| WO | WO 2004/112693 | 12/2004 |
| WO | WO 2005/025606 | 3/2005 |
| WO | WO 2005/032467 | 4/2005 |
| WO | WO 2005/084364 | 9/2005 |
| WO | WO 2005/117927 | 12/2005 |
| WO | WO 2006/002646 | 1/2006 |
| WO | WO 2006/014349 | 2/2006 |
| WO | WO 2006/014466 | 2/2006 |

OTHER PUBLICATIONS

Agnello et al., 2002, "Erythropoietin exerts an anti-inflammatory effect on the CNS in a model of experimental autoimmune encephalomyelitis," Brain Research, vol. 952, pp. 128-134.

Akhtar et al., 1999, "Conformational study of N(epsilon)-(carboxymethyl)lysine adducts of recombinant alpha-crystallins," Current Eye Research, vol. 18:270-276.

Alafaci et al., 2000, "Effect of Recombinant Human Erythropoietin on Cerebral Ischemia Following Experimental Subarachnoid Hemorrhage," Eur. J. Phar., 406:219-225.

Anagnostou et al., 1994, "Erythropoietin receptor mRNA expression in human endothelial cells", Proc. Natl. Acad. Sci. USA 91:3974-3978.

Annable et al., 1972, "The Second International Reference Preparation of Erythropoietin, Human, Urinary, for Bioassay," Bull. Org. mond. Sante, 47:99-112.

Arzneimittelkommission Der Deutschen Arzteschaft, 2004, "Empfehlungen zur Therapie der Demenz," Arzneiverordrung in der Praxis, Band 31, Sonderheft 4 (w/English abstract).

Ashwell et al., 1978, "A Protein from Mammalian Liver that Specifically Binds Galactose-Terminated Glycoproteins," Meth. Enzymol., 50:287-291.

Ay et al., 1999, "Potential usefullness of basic fibroblast growth factor a a treatment for stroke," Cerebrovascular Disease, vol. 9:131-135.

Bany-Mohammed et al., 1996, "Recombinant human erythropoietin: possible role as an antioxidant in premature rabbits," Pediatric Res., vol. 40(3):381-387.

Barber D.L., et al., 2001, "De novo design of cytokine-based alpha helical binding domains display cytotoxic activity," Blood , vol. 98(11. part 2):132b-133b Abstract 4193.

Barber et al.,1994, "Erythropoietin and interleukin-2 activate distinct JAK kinase family members," Mol. Cell. Biol. 14(10):6506-6514.

Barbone et al., 1997, "Mutagenesis studies of the human erythropoietin receptor. Establishment of structure-function relationships," J. Biol. Chem. 272(8):4985-4992.

Barron et al., 1994, "Alternatively spiced mRNAs encoding soluble isoforms of the erythropoietin receptor in murine cell lines and bone marrow," Gene, vol. 147, pp. 263-268.

Baskaya et al., 1997, "The biphasic opening of the blood-brain barrier in the cortex and hippocampus after traumetic brain injury in rats," Neuroscience Letters, vol. 226:33-36.

Bauer, 1995, "The Oxygen Sensor That Controls EPO Production: Facts and Fancies," J. Perinat. Med., 23:7-12.

Bazan, 1989, "A novel family of growth factor receptors: a common binding domain in the growth hormone, prolactin, erythropoietin and IL-6 receptors, and the p75 IL-2 receptor beta-chain," Biochem. Biophys. Res. Commun. 164(2):788-795.

Belayev et al., 1996, "Quantative evaluation of blood-brain barrier permeability following middle cerebral artery occulsion in rats," Brain Research, vol. 739:88-96.

Benit et al., 1993, "The 'WS motif' common to *v-mpl* and members of the cytokine receptor superfamily is dispensable for myeloproliferative leukemia virus pathogenicity," Oncogene 8787-790.
Benjamin et al., 1998, "A plasticity window for blood vessel remodelling is defined by pericyte coverage of the preformed endothelial network and is regulated by PDGF-B and VEGF," Development, vol. 125, pp. 1591-1598.
Benyo et al., 1999, "Expression of erythropoietin receptor by trophoblast cells in the human placenta", Biol. Reproduct. 60:861-870.
Bernat et al., 2003, "Determination of the energetics governing the regulatory step in growth hormone-induced receptor homodimerization," PNAS vol. 100(3):952-57.
Bernaudin et al., 1999, "A potential role for erythropoietin in focal permanent cerebral ischemia in mice", J. Cereb. Blood Flow Metab. 19:643-651.
Bernaudin et al., 2000, "Neurons and astrocytes express EPO mRNA: oxygen-sensing mechanisms that involve the redox-state of the brain", Glia 30:271-278.
Besarab et al., 1998, "The effects of normal as compared with low Hematocrit values in patients with cardiac disease who are receiving hemodialysis and Epoietin," New England Journal of Medicine, vol. 339(9):584-590.
Bianchi et al., 2004, Erythropoietin both protects from and reverses experimental diabetic neuropathy, PNAS, vol. 101, pp. 823-828.
Bickel et al., 1993, "Pharmacologic effects in vivo in brain by vector-mediated peptide drug delivery," Proc Natl Acad Sci U S A. vol. 90:2618-22.
Bickel et al., 1994, In vivo demonstration of subcellular localization of anti-transferrin receptor monoclonal antibody-colloidal gold conjugate in brain capillary endothelium. J Histochem Cytochem. vol. 42(11):1493-7.
Boissel et al., 1993 "Erythropoietin structure-function relationships," J. Biol. Chem. vol. 268(21):15983-15993.
Boado et al., 1998, Drug delivery of antisense molecules to the brain for treatment of Alzheimer's disease and cerebral AIDS. J Pharm Sci. vol. 87(11):1308-15.
Boger and Goldberg, 2001, "Cytokine receptor dimerization and activation: prospects for small molecule agonists," Bioorg. & Med. Chem., 9:557-562.
Bogoyevitch, 2004, "An update on the cardiac effects of erythropoietin cardioprotection by erythropoietin and the lessons learnt from studies in neuroprotection," Cardiovascular Research, vol. 63, pp. 208-216.
Bondy, 1995, "Minireview—The relaxation of oxidative stress and hyperexcitation to neurological disease," Society for Experimental Biology & Medicine, pp. 337-345.
Bonsi et al., 1997, "An erythroid and megakaryocytic common precursor cell line (B1647) expressing both c-mpl and erythropoietin receptor (Epo-R) proliferates and modifies globin chain synthesis in response to megakaryocyte growth and development factor (MGDF) but not to erythropoietin (Epo)," Br. J. Haematol. 98:549-559.
Boudot et al., 1999, "Erythropoietin induces glycosylphosphatidylinositol hydrolysis. Possible involvement of phospholipase c-gamma(2)," J. Biol. Chem. 274(48):33966-33972.
Briggs et al., 1974, "Hepatic Clearance of Intact and Desialylated Erythropoietin," Am. J. Physiol., 227(6):1385-1388.
Brines et al., 2000, "Erythropoietin crosses the blood-brain barrier to protect against experimental brain injury", Proc. Natl. Acad. Sci. USA 97(19):10526-10531.
Brizzi et al., 1991, "Hematopoietic growth factor receptors," Int. J. Cell. Cloning 9:274-300.
Bruneval et al., 1993, "Erythropoietin Synthesis by Tumor Cells in a Case of Meningioma Associated With Erythrocytosis," Blood, 81(6):1593-1597.
Buemi et al., 2002, "Recombinant human erythropoietein influences revascularization and healing in a rat model of random ischaemic flaps," Acta Derm Venereol., vol. 82:411-417.
Bundgaard and Moller, 1981, "Horseradish peroxidase and microperoxidase. Their purity and binding to serum proteins," The Journal of Histochemistry (Abstract) www.jhc.org/cgi.contents/abstract/29/3/331.
Camiscoli et al., 1968, "Comparative Assay of Erythropoietin Standards," Annals New York Acad. Sci., 149:40-45.
Campana et al., 1998, "Identification of a neurotrophic sequence in erythropoietin", Int. J. Mol. Med. 1:235-241.
Caravella et al., 1996, "A partial model of the erythropoietin receptor complex," Proteins 24:394-401.
Cardin et al., 2003, "Evolution of the atrial fibrillation substrate in experimental congestive heart failure: angiotensin-dependent and -independent pathways," Cardiovasc Res. 60(2): 315-325.
Cerneus et al., 1991, "Apical and basolateral transferrin receptors in polarized BeWo cells recycle through separate endosomes," J Cell Biol. vol. 114(6):1149-58.
Chin et al., 2000, "Production and processing of erythropoietin receptor transcripts in brain," Mol Brain Res, vol. 81, pp. 29-42.
Claus-Walker et al., 1984, "Spinal Cord Injury and Serum Erythropoietin," Arch. Phys. Med. Rehabil., 65:370-374.
Cotes et al., 1961, "Bio-Assay of Erythropoietin in Mice Made Polycythaemic By Exposure to Air at a Reduced Pressure," Nature, 191:1065-1067.
Cotes et al., 1966, "The International Reference Preparation of Erythropoietin," Bull. Org. mond. Sante, 35:751-760.
Cotes, 1968, "Quantitative Estimation of Erythropoietin," Part I. Assay and Standardization of Erythropoietin, Annals New York Acad. Sci., 149:12-17.
Cunningham et al., 1989, "High-resolution epitope mapping of hGH-receptor interactions by alanine-scanning mutagenesis," Science, vol. 244:1081-1085.
Cuzzocrea et al., 2005, "Erythropoietin reduces the degree of arthritis caused by type II collagen in the mouse," Arthritis & Rheumatism, vol. 52(3):940-950.
D'Andrea et al., 2000, "A model for assembly and activation of the GM-CSF, IL-3 and IL-5 receptors: insights from activated mutants of the common beta subunit," Exp. Hematol. 28(3):231-243.
D'Andrea et al., 1998, "Dysregulated hematopoiesis and a progressive neurological disorder induced by expression of an activated form of the human common beta chain in transgenic mice," J. Clin. Invest. 102(11):1951-1960.
Dale et al., 2002, "Stimulated platelets use serotonin to enhance their retention of procoagulant proteins on the cell surface," Nature, vol. 415, pp. 175-179.
Dame et al., 2001, "The biology of erythropoietin in the central nervous system and its neurotrophic and neuroprotective potential," Biology of the Neonate, 79(304):228-35.
D'Andrea and Zon. 1990, "Erythropoietin receptor. Subunit structure and activation," J. Clin. Invest. 86(3):681-687.
Deguchi et al., 1999, Retention of biologic activity of human epidermal growth factor following conjugation to a blood-brain barrier drug delivery vector via an extended poly(ethylene glycol) linker. Bioconjug Chem. vol. 10(1):32-7.
Del Mastro et al., 1998, "Strategies for the use of epoetin alfa in breast cancer patients," The Oncologist, Vol. 3:314-318.
Denizot and Lang, 1986, "Rapid colorimetric assay for cell growth and survival—Modifications to the tetrazolium dye procedure giving improved sensitivity and reliability," J. Immul Methods, vol. 89:271-277.
Diaz-Brinton et al., 1998, "Advances and challenges in the prevention and treatment of Alzheimer's disease," Pharm. Res. 15(3):386-98.
Stenesh, J., 1989, Dictionary of Biochemistry And Molecular Biology, $2^{nd}$ Ed., New York, John Wiley & Sons, p. 122, p. 508.
Diem et al., 2005, "Combined therapy with methylprednisolne and erythropoietin in a model of multiple sclerosis," Brain, vol. 128, pp. 375-385.
Dietrich et al., 1993, "Microvascular and neuronal consequences of common carotid artery thrombosis and platelet embolization in rats," J. of Neuropathology and Experimental Neurology, vol. 52(4):351-360.
Digicaylioglu et al. 1995, "Localization of specific erythropoietin binding sites in defined areas of the mouse brain.", Proc. Natl. Acad. Sci. USA 92:3717-3720.
Dipaolo et al., 1992, "Effects of uremia and dialysis on brain electrophysiology after recombinant erythropoietin treatment", ASAIO J. 38:M477-M480.

Dispersyn et al. 1999, Cardiomyocyte remodelling during myocardial hibernation and atrial fibrillation: prelude to apoptosis. Cardiovasc Res. 43(4): 947-957.

Dobbin et al., 1989, "Transient blood-brain barrier permeability following profound temporary global ischaemia: an experimental study using $^{14}$C-AIB," J. of Cerebral Blood Flow Metabolism, vol. 9, pp. 71-78.

Dong et al., 1992, "Receptor binding of asialoerythropoietin," J. Cell. Biochem. 48(3):269-76.

Dordal et al., 1985, "The Role of Carbohydrate in Erythropoietin Action," Endocrinol., 116(6):2293-2299.

Dox et al., 1993, "The Harper Collins Illustrated Medical Dictionary," Harper Collins Publishers, Inc. New York, 1993.

Dube et al, 1988, "Glycosylation at Specific Sites of Erythropoietin is Essential for Biosynthesis, Secretion, and Biological Function," J. Biol. Chem., 263(33):17516-17521.

Eckart 2002, "Anaemia of critical illness—implications for understanding and treating rHuEPO resistance," Nephrol Dial Transplant, vol. 17, Suppl 5, pp. 48-55.

Egrie et al., 2001, "Development and characterization of novel erythropoiesis stimulating protein (NESP)," Neph Dialysis Trans vol. 16 Suppl. 3, pp. 3-13.

Ehrenreich et al., 2002, "Erythropoietin therapy for acute stroke is both safe and beneficial", Molec. Med. 8(8):495-505.

Ehrenreich, 2004, "Erythropoietin: a candidate compound for neuroprotection in schizophrenia," Molecular Psychiatry, 9:42-54.

Ehrenreich. 2004 "A boost for translational neuroscience," Science. vol. 305:184-185.

Elliott et al., 1997, "Mapping of the active site of recombinant human erythropoietin," Blood 89(2):493-502.

Emir, 2004, "Erythropoietin on *bcl-2* gene expression in rat cardiac myocytes after traumatic brain injury," Transplantation Proceedings, vol. 36, pp. 2935-2938.

Erbayraktar et al., 2003, "Asialoerythropoietin is a nonerythropoietic cytokine with broad neuroprotective activity in vivo," Proc. Natl. Acad. Sci. U. S. A. I00(11):6741-6.

Erbayraktar et al., 2006, "Carbamylated erythropoietin reduces radiosurgically-induced brain injury," www.molmed.org. Jul. 2006.

Eur. Pharmacopoeia, 1997, Sainte-Ruffine, France, Maisonneuve p. 5.

Eur. Pharmacopoeia, Strasbourg, Council of Europe, Suppl. 2001, pp. 777-782.

Fantacci et al. 2006, "Carbamylated erythropoietin ameliorates the metabolic stress induced in vivo by severe chronic hypoxia," PNAS, vol. 103(46):17531-17536.

Farrell et al., 2001, "Erythropoietin crosses the blood brain barrier", Blood 98:148b (abstr. # 4265; 43rd Annual Meeting of the American Society of Hematology, Orlando FL, Dec. 7-11, 2001).

Faruki and Kiss, 1995, Erythropoietin, transfusion medical update, The institute for Transfusion Medicine, path.upmc.edu/consult/ria/july 1995.html.

FDA Alert; Nov. 16, 2006, updated Feb. 16, 2007 and Mar. 9, 2007, http://www,FDA.gov.CDER/DRUG/InfoSheets/HCP/RHE2007.HCP.htp.

Feigin et al., 2002, "Recent advances in Huntington's disease: implications for experimental therapeutics," Curr. Opin. Neurol. 15(4):483-9.

Fishbein et al. 1981, "Early phase acute myocardial infarct size quantification: validation of the triphenyl tetrazolium chloride tissue enzyme staining technique," Am Heart Journal. vol. 101(5): 593-600.

Foresta et al., 1994, "Erythropoietin stimulates testosterone production in man," J. of Clinical Endocrinology and Metabolism, vol. 78(3):753-756.

Frank, 2002, "Minireview: Receptor dimerization in GH and erythropoietin action—it takes two to tango, but how?" Endocrinology 143(1):2-10.

Freshney, R.I., 1983, "Culture of animal cells," A Manual of Basic Technique, pp. 3-4, A R. Liss, Inc. NY 1983.

Friden P. M., 1996, "Utilization of an endogenous cellular transport system for the delivery of therapeutics across the blood-brain barrier," J. Controlled Release, vol. 46:117-28.

Friedman et al., 1995, "Erythropoietin in diabetic macular edema and renal insufficiency," American Journal of Kidney Disease, vol. 26(1), pp. 202-208.

Fujita et al., 1997, "Role of alternative splicing of the rat erythropoietin receptor gene in normal and erythroleukemia cells," Lukemia, 11 Supl 3, pp. 444-445.

Fukuda et al., 1989, "Survival of Recombinant Erythropoietin in the Circulation: The Role of Carbohydrates," Blood, 73(1):84-89.

Fung et al., 1990, "The human interleukin-2 receptor: insights into subunit structure and growth signal transduction," Semin. Immunol. 2:119-128.

Gaertner et al., 1994, "Chemo-enzymic backbone engineering of proteins," J. of Biological Chemistry, vol. 269(10):7224-7230.

Garcia et al., 1996, "Ischemic stroke and incomplete infarction," Stroke, vol. 27(4):761-765.

Garthoff, 1995, "Safety and Efficacy Testing of Hormones and Related Products," The Report and Recommendations of ECVAM Workshop 9, A.T.L.A., 23:699-711.

Genbank No. M59941, 1994.

Golberg et al., 2002, "Erythropoietin mimetics derived from solution phase combinatorial libraries," J. Amer. Chem Soc., vol. 124(4):544-555.

Goldwasser et al., 1975, "Erythropoietin: Assay and Study of Its Mode of Actio," Methods in Enzymology, Hormone Action Part B, Peptides Hormones, 1975 Academic Press, vol. 28, pp. 109-121.

Goldwasser et al., 1974, "On the Mechanism of Erythropoietin-Induced Differentiation," XIII. The Role of Sialic Acid in Erythropoietin Action, J. Biol. Chem., 249(13):4202-4206.

Goldwasser et al., 1975, "An Assay for Erythropoietin in Vitro at the Milliunit Level," Endo., 97(2):315-323.

Gorio et al., 2002, "Recombinant human erythropoietin counteracts secondary injury and markedly enhances neurological recovery from experimental spinal cord trauma", Proc. Natl. Acad. Sci. USA 99(14):9450-9455.

Gorio et al., 2005, "Methylprednisolone neutralizes the beneficial effects of erythropoietin in experimental spinal cord injury," PNAS, vol. 102(45):16379-84.

Grasso et al., 2002, "Beneficial effects of systemic administration of recombinant human erythropoietin in rabbits subjected to subarachnoid hemorrhage", Proc. Natl. Acad. Sci. USA 998):5627-5631.

Green, 1998, "Clomethiazole (Zendra® ) in acute ischemic stroke: Basic pharmacology and biochemistry and clinical efficacy," Pharm. Ther. vol. 80(2):123-147.

Greenberg et al. 1995, Congestive heart failure and sleep apnoea-possible mechanisms and effect of CPAP therapy. J Sleep Res. 4(S1): 130-134.

Gregory et al., 1999, "GATA-1 and erythropoietin cooperate to promote erythroid cell survival by regulating bcl-$x_L$ expression", Blood 94:87-96.

Grimm et al., 1990, "Improvement of brain function in hemodialysis patients treated with erythropoietin", Kidney Intl. 38:480-486.

Grimm et al., 2002, "HIF-1-induced erythropoietin in the hypoxic retina protects against light-induced retinal degeneration," Nature Medicine, vol. 8(7):718-724.

Grotzinger, 2002, "Molecular mechanisms of cytokine receptor activation," Biochim. Biophys. Acta. 1592:215-223.

Gruber et al., 2002, "The thrombin mutant W215A/E217A shows safe and potent anticoagulant and antithrombotic effects in vivo," J. Biol. Chem. vol. 277(31):27581-27584.

Gunasekar et al., 2001, "Mechanisms of the apoptotic and necrotic actions of trimethyltin in cerebellar granule cells," Toxicological Sciences. vol. 64:83-89.

Hammond et al., 1968, "Production, Utilization and Excretion of Erythropoietin: I. Chronic Anemias. II. Aplastic Crisis. III. Erythropoietic Effects of Normal Plasma," Annals NY Academy of Sciences 149:516-527.

Hanazono et al., 1995, "Erythropoietin induces tyrosine phosphorylation of the beta chain of the GM-CSF receptor," Biochem. Biophys. Res. Comm. 208(3):1060-1066.

Hancher et al., 1974, "Recovery of Erythropoietin from Anemic Sheep Plasma," Biotechnology and Bioengineering. vol. 16:1069-1079.

Hansen, et al., 2000, "A randomized, blinded placebo controlled, phase II, dose-finding study of ARANESP in patients with lymphoproliferative malignances," Blood, vol. 96(11), pp. 155b.

Harris et al. 1992, "Ligand binding properties of the human erythropoietin receptor extracellular domain expressed in *Escherichia coli*," J. Biol. Chem. 267(21):15205-15209.

Harris K.W. et al., 2000, "Purification and characterization of yeast-expressed erythropoietin (R 103 A), an erythropoietin antagonist," Blood 96(11, part 2):154b Abstract 4366.

Harris K.W. et al., 2001, "Characterization of the yeast-expressed erythropoietin mutant, Epo (R 103 A), a specific inhibitor of human primary hematopoietic cell erythropoiesis," Blood, 98(11, part 1):77a Abstract 319.

Harris K.W., 2004, "Signal transduction in myeloid differentiation," Federal Research in Progress database, FRP 03-05, ID No. 136456, Comp & Dist. By NTIS.

Hassan et al., 1995, "Review of megakaryoblastic cell lines -Characteristic biological features of human megakaryoblastic leukaemia cell lines," Leuk. Res. 19(9):589-594.

Hefti, 1997, "Pharmacology of neurotrophic factors", Annu. Rev. Pharmacol. Toxicol. 37:239-267.

Hengemihle et al., 1996, "Chronic treatment with human recombinant erythropoietin increases hematocrit and improves water maze performance in mice", Physiol. Behav. 59(1):153-156.

Hirakata et al., 1992, "CBF and oxygen metabolism in hemodialysis patients: effects of anemia correction with recombinant human EPO", Am. J. Physiol. 262:F737-F743.

Horton et al., 1991, "Von Hippel-Lindau Disease and Erythrocytosis: Radioimmunoassay of Erythropoietin in Cyst Fluid From a Brainstem Hemangioblastoma," Neurology, 41:753-754.

Huwyler and Pardridge, 1998, Examination of blood-brain barrier transferrin receptor by confocal fluorescent microscopy of unfixed isolated rat brain capillaries. J Neurochem. 70(2):883-6.

Huwyler et al., 1997, "Receptor mediated delivery of daunomycin using immunoliposomes: pharmacokinetics and tissue distribution in the rat," J Pharmacol Exp Ther. vol. 282(3):1541-6.

Imada et al., 1992, "Interleukin-2 (IL-2) induces erythroid differentiation and tyrosine phosphorylation in ELM-I-1 cells transfected with a human IL-2 receptor beta chain cDNA," Biochem. Biophys. Res. Commun. 188(1):352-357.

Imai et al., 1990, "Physicochemical and Biological Characterization of Asialoerythropoietin," Eur. J. Biochem., 194:457-462.

Iseki et al., 1996, "Increased risk of cardiovascular disease with erythropoietin in chronic dialysis patients," Nephron, vol. 72, pp. 30-36.

Itoh et al., 1990, "Cloning of an interleukin-3 receptor gene: a member of a distinct receptor gene family," Science 247:324-327.

Jenkins et al., 1999, "A cell type-specific constitutive point mutant of the common beta-subunit of the human granulocyte-macrophage colony-stimulating factor (GM-CSF), interleukin (IL)-3. and IL-5 receptors requires the GM-CSF receptor alpha-subunit for activation," J. Biol. Chem. 274(13):8669-8677.

Jiang et al., 1996, "Delayed intravenous administration of basic fibroblast growth factor (bFGF) reduces infarct volume in a model of focal cerebral ischemia/reperfusion in the rat," J of Neurological Sciences, vol. 139:173-179.

Jones et al., 1990, "Human erythropoietin receptor: cloning, expression, and biologic characterization," Blood 76(1):31-35.

Jooss et al., 1996, "Cyclophosphamide diminishes inflammation and prolongs transgene expression following delivery of adenoviral vectors to mouse liver and lung," Hum. Gene Ther. 7(13):1555-66.

Josse et al., 1999, "Tryptophan residue(s) as major components of the human serum paraoxonase active site," Chem Biol Interact, vol. 119-120:79-84.

Josse et al., 1999, "Human serum paraoxanase (PON1): Identification of essential amino acid residues by group-selective labelling and site-directed mutagenesis," Chem Biol Interact, vol. 119-120:71-78.

Jubinsky et al., 1996, "The beta c component of the granulocyte-macrophage colony-stimulating factor (GM-CSF)/interleukin 3 (IL-3)/IL-5 receptor interacts with a hybrid GM-CSF/erythropoietin receptor to influence proliferation and beta-globin mRNA expression," Mol. Med. 2(6):766-773.

Jubinsky et al., 1997, "The beta chain of the interleukin-3 receptor functionally associates with the erythropoietin receptor," Blood 90(5):1867-1873.

Junk et al., 2002, "Erythropoietin administration protects retinal neurons from acute ischemia-reperfusion injury", Proc. Natl. Acad. Sci. USA 99(16):10659-10664.

Juul et al., 1998, "Erythropoietin and erythropoietin receptor in the developing human central nervous system", Pediatr. Res. 43(1):40-49.

Juul et al., 1998, "Tissue distribution of erythropoietin and erythropoietin receptor in the developing human fetus", Early Human Devel. 52(3):235-249.

Juul et al., 2001, "Recombinant erythropoietin (EPO) crosses the blood brain barrier (BBB) in preterm fetal sheep", Soc. for Neuroscience Abstracts 27(1):929 (31st Annual Meeting of the Society for Neuroscience, San Diego, CA Nov. 10-15, 2001).

Juul, S. 2002, "Erythropoietin in the central nervous system, and its use to prevent hypoxic-ischemic brain damage," Acta Paediatr. Supp. vol. 438, pp. 36-42.

Kang et al., 1994, "Pharmacokinetics and saturable blood-brain barrier transport of biotin bound to a conjugate of avidin and a monoclonal antibody to the transferrin receptor," Drug Metab Dispos. vol. 22(1):99-105.

Kawasaki et al., 2001, "Structural analysis of sulfated N-linked oligosaccharides in erythropoietin," Glycobiology, vol. 11(12):1043-1049.

Kaye DM et al., 2003, Feasibility and short-term efficacy of percutaneous mitral annular reduction for the therapy of heart failure-induced mitral regurgitation. Circulation 108:1795-1797.

Keighley, 1968, "Further Experiences with Assays, Units, and Standards of Erythropoietin," Annals New York Acad. Sci., 149:18-24.

Keswani et al., 2004, "A novel endogenous erythropoietin mediated pathway prevents axonal degeneration," Ann. Neurol. vol. 56(6):815-826.

Kirito et al., 2002, "Identification of the human erythropoietin receptor region required for Stat1 and Stat3 activation," Blood 99(1):102-110.

Kishimoto et al., 1987, "Transendothelial transport (transcytosis) of iron-transferrin complex in the rat liver," Am J Anat. vol. 178:241-9.

Kitajima et al., 1994, "Effective combination therapy by recombinant erythropoietin and cepharanthin in a girl with refractory anemia," Japanese J. Clin. Hematology. vol. 35(7):694-6988 (w/English abstract).

Kitamura et al., 1989, "Identification and analysis of human erythropoietin receptors on a factor-dependent cell line, TF-1," Blood. vol. 73(2):375-80.

Kohama et al., 2000, "Large Uterine Myoma with Erythropoietin Messenger RNA and Erythrocytosis," Obstetrics and Gynecology, 96(5):826-828.

Konishi et al., 1993, "Trophic effect of erythropoietin and other hematopoietic factors on central cholinergic neurons in vitro and in vivo", Brain Res. 609:29-35.

Kopf et al., 1994, "Memory improving actions of glucose: involvement of a central cholinergic muscarinic mechanism.", Behav. Neural Biol. 62:237-243.

Gabriel et al., 1998, "High-dose recombinant human erythropoietin stimulates reticulocyte production in patients with multiple organ dysfunction syndrome," J of Trauma, vol. 44(2):361-367.

Kumral et al., 2004, "Erythropoietin improves long-term spatial memory deficits and brain injury following neonatal hypoxia-ischemia in rat," Behavioral Brain Research, vol. 153:77-86.

Kuroiwa et al., 1985, "The biphasic opening of the blood-barrier to proteins following temporary middle cerebral artery occlusion," Acta Neurophotalogica, vol. 68:122-129.

Lai et al., 1996, "The molecular role of the common gamma $_c$ subunit in signal transduction reveals functional asymmetry within multimeric cytokine receptor complexes." Proc. Natl. Acad. Sci. USA 93:231-235.

Latini et al., 1998, "Comparative efficacy of a DA2/$\alpha$2 agonist and a $\beta$ blocker in reducing adrenergic drive and cardiac fibrosis in an experimental model of left ventricular dysfunction after coronary artery occlusion", J. Cardiovasc. Pharmacol. 31(4):601-608.

Lee P et al. 1998, Conditional lineage ablation to model human diseases. Proc Natl Acad Sci U S A. 95:11371-11376.
Leist et al., 2004, "Derivatives of erythropoietin that are tissue protective but not erythropoietic," Science, vol. 305, pp. 239-242.
Lewis et al., 1996, "Molecular characterization of the 7q deletion in myeloid disorders," Br. J. Haematol. 93:75-80.
Lewis et al., 2004, "Opposing effects of P13 kinase pathway activation on human myeloid and erythroid progenitor cell proliferation and differentiation in vitro," Exp. Hematol. 32:36-44.
Li et al., 1996, "Erythropoietin receptors are expressed in the central nervous system of mid-trimester human fetuses", Pediatr. Res. 40(3):376-380.
Li et al., 1998, "A single pre training glucose injection induces memory facilitation in rodents performing various tasks: contribution of acidic fibroblast growth factor", Neurosci. 85(3):785-794.
Life Extension- Wound Healing; Wound: from the old english word wund, http:/www.lef.org/protocols/prtcls-txt/t-prtcl-1 1 1.html Sep. 23, 2004, pp. 1-12, 2004.
Linsley et al., 1994, "Applications of electrospray mass spectrometry to erythropoietin *N*- and *O*-linked glycans," Anal. Biochem. 219:207-217.
Lipinski et al., 1995, "Nerve growth factor facilitates conditioned taste aversion learning in normal rats", Brain Res. 692:143-153.
Liu et al., 1994, "Multiple cytokines stimulate the binding of a common 145-kilodalton protein to Shc at the Grb2 recognition site of Shc." Mol. Cell. Biol. 14(10):6926-6935.
Liu et al., 1994, "Tissue specific expression of human erythropoietin receptor in transgenic mice", Devel. Biol. 166:159-169.
Liu et al., 1996, "Transgenic mice containing the human erythropoietin receptor gene exhibit correct hematopoietic and neural expression", Proc. Assoc. Am. Physicians 108(6):449-454.
Liu et al., 1997, "Regulated human erythropoietin receptor expression in mouse brain", J. Biol. Chem. 272(51):32395-32400.
Liu et al., 2007, "A potent erythropoietin-mimicking human antibody interacts through a novel binding site," Blood, vol. 110(7):2408-2413.
Livnah et al., 1999, "Crystallographic evidence for preformed dimers of erythropoietin receptor before ligand activation," Science 283:987-990.
Loberg et al., 1993, "Neuronal uptake of plasma proteins after transient cerebral ischemia/hypoxia," APMIS, vol. 101:777-783.
Lowy et al., 1960, "Inactivation of Erythropoietin by Neuraminidase and by Mild Substitution Reactions," Nature, 185:102-103.
Lu et al., 2005, "Erythropoietin enhances neurogenesis and restores spatial memory in rats after traumatic brain injury," J. of Neurotrauma, vol. 22(9), pp. 1011-1017.
Magnanti et al., 2001, "Erythropoietin expression in primary rat Sertoli and peritubular myoid cells," Blood, vol. 98(9):2872-2874.
Marrero et al., 1998, "Erythropoietin receptor-operated $Ca^{2+}$ channels: activation by phospholipase C-γ1", Kidney Intl. 53:1259-1268.
Marsh et al., 1991, "rHuEPO treatment improves brain and cognitive function of anemic dialysis patients", Kidney Intl. 39:155-163.
Marti et al., 1996, "Erythropoietin gene expression in human, monkey and murine brain", Eur. J. Neurosci. 8:666-676.
Marti et al., 1997, "Detection of erythropoietin in human liquor: intrinsic erythropoietin production in the brain", Kidney Intl. 51:416-418.
Massague, 1987, "The TGF-beta family of growth and differentiation factors," Cell., vol. 49:437-8.
Masuda et al., 1993, "Functional erythropoietin receptor of the cells with neural characteristics. Comparison with receptor properties of erythroid cells", J. Biol. Chem. 268(15):11208-11216.
Masuda et al., 1994, "A novel site of erythropoietin production. Oxygen dependent production in cultured rat astrocytes", J. Biol. Chem. 269(30):19488-19493.
Masuda et al., 1997, "Insulin like growth factors and insulin stimulate erythropoietin production in primary cultured astrocytes", Brain Res. 746:63-70.
Matsuyama et al., 2000, "Erythrocytosis Caused by an Erythropoietin-Producing Hepatocellular Carcinoma," J. Surg. Oncology, 75:197-202.
Matthews et al., 1996, "A sequential dimerization mechanism for erythropoietin receptor activation," PNAS, USA 93:9471-9476.
McClure et al., 2001, "GM-CSF binding to its receptor induces oligomerisation of the common beta-subunit," Cytokine 13(4):240-243.
Means et al., 1996, "Inhibition of human erythroid colony-forming units by interferons alpha and beta: differing mechanisms despite shared receptor," Exp. Hematol. 24:204-208.
Menzies and Ellis, 1990 Intestinal obstruction from adhesions—how big is the problem?, Ann. R. Coll. Surg. Engl., vol. 72:60-3.
Menzies et al., 1990, "Extravastatin of albumin in ischaemia brain oedema," Acta Neurochirurgica, Suppl. vol. 51:220-222.
Mioni et al., 1992, "Evidence for specific binding and stimulatory effects of recombinant human erythropoietin on isolated adult rat Leydig cells", Acta Endocrinologica 127:459-465.
Mitsuma, et al., 2006, "Cardioprotective effects of recombinant human erythropoietin in rats with experimental autoimmune myocarditis," Biochemical and Biophysical Research Communications, vol. 344:987-994.
Miu et al., 2004, "Have no fear, erythropoietin is here, erythropoietin protects fear conditioning performances after functional inactivation of the amygdala," Behavioral Brain Research, vol. 155, pp. 223-229.
Miyake et al., 1977, "Purification of Human Erythropoietin," J. Biol. Chem., 252(15):5558-5564.
Mogensen et al., 2004, Erythropoietin improves place learning in fimbria-fornix-transected rats and modifies the search pattern of normal rats, Pharmacology, Biochemistry and Behavior, vol. 77:381-390.
Morell et al., 1968, "Physical and Chemical Studies on Ceruloplasmin," Metabolic Studies on Sialic Acid-Free Ceruloplasmin In Vivo, J. Biol. Chem., 243(1):155-159.
Morishita et al., 1997, "Erythropoietin receptor is expressed in rat hippocampal and cerebral cortical neurons, and erythropoietin prevents in vitro glutamate induced neuronal death", Neurosci. 76:105-116.
Moss et al., 1996, "Oxygen administration enhances memory formation in healthy young adults", Psychopharmacol. 124:255-260.
Mun et al., 2000, "Impaired biological activity of erythropoietin by cyanate carbamylation," Blood Purif. 18:13-7.
Murakami et al., 1991, "Critical cytoplasmic region of the interleukin 6 signal transducer gp130 is conserved in the cytokine receptor family," Proc. Natl. Acad. Sci. USA 88(24):11349-11353.
Murray, 1996, Harpers Illustrated Biochemistry $26^{th}$ ed. pp. 524-526, McGraw-Hill Co.
Nagao et al., 1992, "Production and ligand-binding characteristics of the soluble form of murine erythropoietin receptor," Biochemical and Biophysical Research Communications, vol. 188(2):888-897.
Nakamura et al., 1998, "Elevated levels of erythropoietin in cerebrospinal fluid of depressed patients", Am. J. Med. Sci. 315(3):199-201.
Naranda et al., 2002, "Activation of erythropoietin receptor through a novel extracellular binding site," Endocrinology 143(6):2293-2302.
Nathan, 1994, "Studies of hybrid hematopoietic growth factor receptors," Stem Cells 12 (Suppl 1):27-35.
Nestler et al., 1985, "Stimulation of rat ovarian cell steroidogenesis by high density lipoproteins modified with tetranitromethrane," J. Biol Chem. vol. 260(12):7316-21.
Nimtz et al., 1993, "Characterization of a phosphorylated oligosaccharide from erythropoeitin expressed in recombinant BHK cells." Glycoconj. J. vol. 10, No. 4, p. 259, S6.7.
Nissenson et al., 1991, "Recombinant human erythropoietin and renal anemia: molecular biology, clinical efficacy and nervous system effects", Ann. Int. Med. 114:402-416.
Nissenson, 1989, "Recombinant human erythropoietin: impact on brain and cognitive function, exercise tolerance, sexual potency and quality of life", Sem. Nephrol. 9(1) suppl.:25-31.
Noguchi et al., 1991, "Cloning of the human erythropoietin receptor gene," Blood 78(10):2548-2556.
Ogden, 1989, "Monitoring considerations in recombinant human erythropoietin therapy", Sem. Nephrol. 9(1):suppl. 2:12-15.
Ohta et al., 2001, "Selective glycopeptide mapping of erythropoietin by on-line high-performance liquid chromatography-electrospray ionization mass spectrometry," J. Chromatography A, 910:1-11.

Okada et al., 1996, "Erythropoietin stimulates proliferation of rat-cultured gastric mucosal cells", Digestion 57:328-332.
On-Line Medical Dictionary Lysozyme entry; website http://cancerweb.ncl.ac.uk/omd. Published at the Dept. of Medical Oncology, University of Newcastle upon Type. Copyright 1997-2004. The CancerWEB Project.
Opitz CF et al. 1995, "Effects of reperfusion on arrhythmias and death after coronary artery occlusion in the rat. Continuous telemetric ECG monitoring in conscious, untethered rats," Circulation. 92(2):253-261.
Opitz CF et al. 1998, "Effects of reperfusion on arrhythmias and death after coronary artery occlusion in the rat: increased electrical stability independent of myocardial salvage," J Am Coll Cardiol. 32(1): 261-267.
Page et al., 1996, "A sensitive human cell line based bioassay for megakaryocyte growth and development factor or thrombopoietin," Cytokine 8(1):66-69.
Pantoliano et al., 1987, "Protein engineering of subtilisin BPN': Enhanced stabilization through the introduction of two cysteins to form a disulfide bond," Biochemistry, vol. 26:2077-2082.
Pardridge et al., 1991, "Selective transport of an anti-transferrin receptor antibody through the blood-brain barrier in vivo", J. Pharmacol. Exp. Ther. vol. 259(1):66-60.
Pardridge WM. 1998, "CNS drug design based on principles of blood-brain barrier transport." J Neurochem. vol. 70:1781-92.
Pardridge, 1997, "Drug delivery to the brain", J. Cerebral Blood Flow Metab. 17(7):713-731.
Park et al., 1997, "Development of an in vitro bioassay system for human thrombopoietin by constructing a recombinant murine cell line expressing human thrombopoietin receptor," Mol. Cells. 7(6):699-704.
Pazur et al., 2000, "Oligosaccharides as immuno-determinants of erythropoietin for two sets of anti-carbohydrates antibodies," J. Protein Chem. vol. 19(8):631-635.
Pedersen et al., 1995, "The interaction of beta 2-microglobulin (beta 2m) with mouse class I major histocompatibility antigens and its ability to support peptide binding. A comparison of human and mouse beta 2m," Eur. J. Immunol. 25:1609-16.
Peng et al., 2000, "HPLC/ESI MS and MALDI/TOF MS analysis of microheterogeneity of the N-linked oligosaccharides of recombinant human erythropoietin," Yao Xue Bao (Acta Pharmaceutica Sinica) 35(10):770-773.
Penny and Forget, 1991, "Genomic organization of the human erythropoietin receptor gene," Genomics 11(4):974-980.
Petito, 1979, "Early and late mechanisms of increased vascular permeability following experimental cerebral infarction," J. Neuropatholo Exp Neurol. vol. 38(3):222-34.
Pfeffer JM et al. 1991, Progressive ventricular remodeling in rat with myocardial infarction. Am J Physiol. 260(5 Pt 2): H1406-1414.
Physicians' Desk Reference, 2000 (Medical Economics Company, Inc. Montvale, NJ), pp. 519-525 and 2125-2131.
Physicians' Desk Reference, 1995, $49^{th}$ Edition (Medical Economics Data Production Company, Montvale, NJ), pp. 1765-1769.
Pilbeam et al., 1993, "Comparison of the effects of various lengths of synthetic human parathyroid hormone-related peptide (hPTHrP) of malignancy on bone resorption and formation in organ culture," Bone, vol. 14:717-720.
Plapp et al., 1971, "Activity of bovine pancreatic deoxyribonuclease A with modified amino groups," J. Biol. Chem. 246(4):939-45.
Poduslo et al., 1994, "Macromolecular permeability across the blood-nerve and blood-brain barriers", Proc. Natl. Acad. Sci. USA 91:5705-5709.
Ponger et al., 1983, "Preparation of high-potency, non-aggregating insulins using a novel sulfation procedure," Diabetes, vol. 32:1087-1091.
Prendergast et al., 1997, "Nitric oxide synthase inhibition impairs spatial navigation learning and induces conditioned taste aversion", Pharmacol. Biochem. Behav. vol. 57:(1/2):347-35257:347-352.
Qui et al., 1998, "Homodimerization restores biological activity to an inactive erythropoietin mutant," J. Biol. Chem. 273(18):11173-11176.
Remick, 2003, "Cytokine therapeutics for the treatment of sepsis: why has nothing worked?" Current Pharmaceutical Design, vol. 9, pp. 1-8.
Remy et al., 1999, "Erythropoietin receptor activation by a ligand-induced conformation change," Science 283:990-993.
Robinson et al., 1975, "Tetanus toxin. The effect of chemical modifications on toxicity, immunogenicity, and conformation," J. Biol. Chem. 250(18):7435-42.
Romanovsky et al., 1996, "First and second phases of biphasic fever: two sequential stages of the sickness syndrome?" The American Physiological Society, pp. R244-R253.
Rose et al., 1998, "Receptor-mediated angiotensin II transcytosis by brain microvessel endothelial cells", Peptides 19(6):1023-1030.
Rosenbaum et al., 1997, "Retinal ischemia leads to apoptosis which is ameliorated by aurintricarboxylic acid," Vis. Res., 37(24):3445-51.
Rush et al., 1993, "Peptide mapping and evaluation of glycopeptide microheterogeneity derived from endoproteinase digestion of erythropoietin by affinity high-performance capillary electrophoresis," Anal. Chem. 65(14):1834-1842.
Rush et al., 1995, "Microheterogeneity of erythropoietin carbohydrate structure," Analytical Chemistry, 67(8):1442-1452.
Sadamoto et al., 1998, "Erythropoietin prevents place navigation disability and cortical infarction in rats with permanent occlusion of the middle cerebral artery", Biochem. Biophys. Res. Comm. 253:26-32.
Saito et al., 1990, "Role of neuroexcitation in development of blood-brain barrier and oedematous changes following cerebral ischaemia and traumatic brain injury," Acta Neurochirurgica, Suppl. vol. 51, pp. 186-188.
Sakanaka et al., 1998, "In vivo evidence that erythropoietin protects neurons from ischemic damage", Proc. Natl. Acad. Sci. USA 95:4635-4640.
Satake et al. 1990, "Chemical modification of erythropoietin: an increase in in vitro activity by guanidination," Biochim. Biophys. Acta. 1038(1):125-9.
Savino et al., 2006, "Delayed administration of erythropoietin and its non-erythropoietic derivatives ameliorates chronic murine autoimmune encephalomyelitis," J. of Neuroimmunology, vol. 172, pp. 27-37.
Sawyer et al., 1989, "Receptors for erythropoietin in mouse and human erythroid cells and placenta", Blood 74(1):103-109.
Schiffl and Lang, 1997, "Hypertension induced by recombinant human erythropoietin (rHU-EPO) can be prevented by indomethacin. Pathogenetic role of cytosolic calcium," Eur J. Med Res. vol. 2:97-100.
Schussler et al., 1998, "Erythropoietin and obstetrical influences," Zeitschrift fur Geburtshilfe und Neonatologie (202)(2), pp. 64-68 (Abstract Only).
Scott et al., 2000, "Reassessment of interactions between hematopoietic receptors using common beta-chain and interleukin-3-specific receptor beta-chain-null cells: no evidence of functional interactions with receptors for erythropoietin, granulocyte colony-stimulating factor, or stem cell factor," Blood 96(4):1588-1590.
Shikama et al., 1996, "A constitutively activated chimeric cytokine receptor confers factor-independent growth in hematopoietic cell lines," Blood 88(2):455-464.
Shiramizu et al., 1994, "Constitutive Secretion of Erythropoietin by Human Renal Adenocarcinoma Cells in Vivo and in Vitro," Exp. Cell Res., 215:249-256.
Shore et al., 1968, "Quantitative Estimation of Erythropoietin," Annals New York Acad. Sci., 149:46-48.
Shulman et al., 2002, "Current drug treatment of Sepsis," Hospital Pharmacist, vol. 9, pp. 97-107.
Silva et al., 1999, "Erythropoietin can induce the expression of Bcl-xL through Stat5 in erythropoietin-dependent progenitor cell lines", J. Biol. Chem. 274(32):22165-22169.
Siren et al., 2001, "Erythropoietin prevents neuronal apoptosis after cerebral ischemia and metabolic stress", Proc. Natl. Acad. Sci. USA 98(7):4044-4049.
Soda et al., 1984, "Transendothelial transport (transcytosis) of iron-transferrin complex in the bone marrow," J Ultrastruct Res. vol. 88(1):18-29.

Spivak et al., 1989, "The In Vivo Metabolism of Recombinant Human Erythropoietin in the Rat," Blood, 73:90-99.
Stark et al., 1960, "Reactions of the Cyanate Present in Aqueous Urea With Amino Acids and Proteins," J. Biol. Chem. 235(11): 3177-3181.
Stark, 1967, "Modification of proteins with cyanate" Methods Enzymol. 11:590-594.
Stedman's Medical Dictionary, 27$^{th}$ Ed. 2000, Lippincott, Williams, and Wilkins: Trauma and Inflammation, pp. 897-898, 1865-1866.
Steece-Collier et al., 2002, "Etiology of Parkinson's disease: Genetics and environment revisited," Proc. Natl. Acad. Sci. U. S. A. 99(22):13972-4.
Storring et al.,1992, "The International Standard for Recombinant DNA-Derived Erythropoietin: Collaborative Study of Four Recombinant DNA-derived Erythropoietins and Two Highly Purified Human Urinary Erythropoietins," J. Endocrinol., 134:459-484.
Storring et al., 1998, "Epoietin Alfa and Beta Differ In Their Erythropoietin Isoform Compositions and Biological Properties," British J. Haematology, 100:79-89.
Sturm et al., 2005, "Recombinant human erythropoietin: effects on frataxin expression in vitro," European J. of Clinical Investigation, vol. 35, pp. 711-717.
Suzuki et al., 1983, "The effects of 5-minute ischemia in Mongolian gerbils: 1. Blood-brain barrier, cerebral blood flow, and local cerebral glucose utilization changes," Acta Neurophatologica (Berl), vol. 60:207-216.
Suzuki et al., 2001, "Erythropoietin Synthesis by Tumour Tissues in a Patient With Uterine Myoma and Erythrocytosis," British J. Haematology, 113:49-51.
Sweeney et al., 1995, "Cellular mechanisms involved in brain ischemia," Can. J. Physiol. Pharmacol. vol. 73:1525-1535.
Swiss Accession No. P32927, Oct. 1, 1993.
Syed et al., 1998, "Efficiency of signaling through cytokine receptors depends critically on receptor orientation," Nature 395:511-516.
Szabo et al., 1998, "Protection against peroxynitrite-induced fibroblast injury and arthritis development by inhibition of poly(ADP-ribose) synthase," Proc. Natl. Acad. Sci. USA, vol. 95, pp. 3867-3872.
Tabira et al., 1995, "Neurotrophic effect of hematopoietic cytokines on cholinergic and other neurons in vitro", Int. J. Devl. Neurosci. vol. 13(3/4):241-252.
Takahashi, 1977, "The reactions of phenylglyoxal and related reagents with amino acids," J. Biochem., vol. 81:395-402.
Teien et al., 1995, Doppler evaluation of severity of mitral regurgitation: relation to pulmonary venous blood flow patterns in an animal study. J Am Coll Cardiol. 25(1): 264-268.
Temple et al., 1995, "Recombinant erythropoietin improves cognitive function in patients maintained on chronic ambulatory peritoneal dialysis," Nephrology Dialysis Transplantation, vol. 10:1733-1738.
Tojo et al., 1987, "Identification of erythropoietin receptors on fetal liver erythroid cells," Biochem. Biophys. Res. Commun. 148(1):443-448.
Urena P. 2002, "Treatment of anemia in chronic renal failure by a long-active activator of erythropoiesis," Press Medicale, vol. 31(11):505-514 (Abstract only).
Van Der Meer et al., 2005, "Erythropoietin induces neovascularization and improves cardiac function in rats with heart failure after myocardial infraction," JACC, vol. 46(11) pp. 125-133.
Vansteenkiste et al., 2003, "Darbepoietin alfa: a new approach to the treatment of chemotherapy-induced anaemia," Expert Opin. Biol. Ther. vol. 3(3):501-508.
Vezanni et al., 1999, "Interleukin-1-β Immunoreactivity and microglia are enhanced in the rat hippocampus by focal kainate application: Functional evidence for enhancement of electrographic seizures," J. Neurosci, vol. 19(12):5054-65.
Vezzani et al., 1986, "Anticonvulsant drugs effective against human temporal lobe epilepsy prevent seizures but not neurotoxicity induced in rats by quinolinic acid: Electroencephalographic, behavioral and histological assessments," J. Pharmacol Exp. Ther. vol. 239(1):256-63.
Vukicevic et al., 1996, "Induction of nephrogenic mesenchyme by osteogenic protein 1 (bone morphogenetic protein 7)," PNAS USA, vol. 93:9021-9026.
Wauben-Penris et al., 1988, "The release of iron by Sertoli cells in culture," Biol Reprod. vol. 38:1105-13.
Weiland et al., 1982, "In vivo Activity of Asialo-Erythropoietin in Combination with Asialo-Glycoproteins," Blut, 44:173-175.
Wells, 1990, "Additivity of mutational effects in proteins," Biochemistry, vol. 29(37):8509-8517.
Wen et al., 1994, "Erythropoietin structure-function relationships," J. Biol. Chem. 269(36):22839-22846.
Westenfelder et al., 1999, "Human, rat and mouse kidney cells express functional erythropoietin receptors", Kidney Intl. 55:808-820.
Widness et al., 1995, "Erythropoietin transplacental passage—Review of animal studies," J. Perinat. Med. vol. 23, pp. 61-70.
Williams et al., 1994, "Human erythropoietin receptor", Ann. NY Acad. Sci. 718:232-244.
Williamson et al., 1993, "Protein and lipid kinase activation cascades in interleukin-2 receptor signalling," Semin. Immunol. 5(5):337-344.
Winkelmann et al., 1990, "The gene for the human erythropoietin receptor: analysis of the coding sequence and assignment to chromosome 19p." Blood 76(1):24-30.
Wit et al., 1992, "Experimental models of ventricular tachycardia and fibrillation caused by ischemia and infarction," Circulation 85 Suppl. 1:I-32-1-42.
Wojchowski and Caslake, 1989, "Biotinylated recombinant human erythropoietins: bioactivity and utility as receptor ligands," Blood, vol. 74(3):952-958.
Wolcott et al., 1989, "Recombinant human erythropoietin treatment may improve quality of life and cognitive function in chronic hemodialysis patients", Am. J. Kidney Dis. 14(6):478-485.
Wolf et al., 1997, "Erythropoietin administration increases production and reactivity of platelets in dogs," Thromb. Haemost. 78:1505-1509.
Wu and Pardridge, 1996, Central nervous system pharmacologic effect in conscious rats after intravenous injection of a biotinylated vasoactive intestinal peptide analog coupled to a blood-brain barrier drug delivery system. J Pharmacol Exp Ther. Oct; 279(1):77-83.
Wu et al., 1999, "Neuroprotection with noninvasive neurotrophin delivery to the brain", PNAS 96:254-259.
Xiao et al., 1998, "Fibrinogen deficiency is compatible with the development of atherosclerosis in mice," J. Clin Invest. vol. 101(5):1184-1194.
Yamaji et al., 1996, "Brain capillary endothelial cells express two forms of erythropoietin receptor mRNA", Eur. J. Biochem. 239:494-500.
Yamamura et al., 1992, "Distinct downstream signaling mechanism between erythropoietin receptor and interleukin-2 receptor," EMBO J. 11(13):4909-4915.
Yang et al., 1994, "Reperfusion-induced injury to the blood-brain barrier after middle-cerebral artery occlusion in rats," Stroke, vol. 25(8):1658-1665.
Yang et al., 2002, "Effects of ammonia and glucosamine on the heterogeneity of erythropoietin glycoforms," Biotechnol. Prog. 18:129-38.
Yet et al, 1993, "The extracytoplasmic domain of the erythropoietin receptor forms a monomeric complex with erythropoietin," Blood 82(6):1713-1719.
Yoshimura et al., 1995, "A novel cytokine-inducible gene CIS encodes an SH2-containing protein that binds to tyrosine-phosphorylated interleukin 3 and erythropoietin receptors," EMBO J. 14(12):2816-2826.
Yoshimura et al., 1996, "Mouse oncostatin M: an immediate early gene induced by multiple cytokines through the JAK-STAT5 pathway," EMBO J. 15(5):1055-1063.
Yoshimura et al., 1996, "Physician Education: The Erythropoietin Receptor and Signal Transduction," Oncologist 1(5):337-339.
Zeng, 1991, "Lysine modification of metallothionein by carbamylation and guanidination," Methods Enzymol. 205:433-7.
Zhang et al., 2006, "Erythropoietin protects CA1 neurons against global cerebral ischemia in rat: potential signaling mechanisms," J. of Neuroscience Research, vol. 83:1241-51.
Zhu et al., 2002, "Detecting and responding to hypoxia," Nephrol. Dial. Transplant. 17 Suppl 1:3-7.
Brines et al., 2004, "Erythropoietin mediates tissue protection through an erythropoietin and commom β-subunit heteroreceptor," PNAS, vol. 101(41):14907-14912.

* cited by examiner serum concentrations following 240 ug LPS

Peripheral Carbamylated EPO vs Central

TISSUE PROTECTIVE CYTOKINES FOR THE TREATMENT AND PREVENTION OF SEPSIS AND THE FORMATION OF ADHESIONS

FIELD OF THE INVENTION

The present invention is directed to a method of treating, preventing, delaying the onset, and/or reducing the effects of sepsis and related complications. In particular, the present invention is directed to the use of tissue protective cytokines for the treatment, prevention, delay, and/or reduction of complications with regard to sepsis, adhesion formation, and organ failure. Furthermore, the tissue protective cytokines of the present invention are also contemplated for treatment, prevention, delay, and/or reduction of complications of general inflammatory conditions resulting from infection.

BACKGROUND OF THE INVENTION

Several strategies exist for responding to infection, immune challenges, inflammation, and trauma in a host. One mechanism by which the host attempts to respond to these challenges is through the upregulation of cytokines, nonantibody proteins that act as intercellular regulators. Some cytokines, known as proinflammatory cytokines, counteract the challenges to the host by enhancing the disease in the hopes of ridding the host of the challenge and host cells damaged by the challenge. Proinflammatory cytokines include, but are not limited to, interleukins (IL), such as IL-1, IL-6, IL-8, and IL-18, and tumor necrosis factor (TNF).

When released, the proinflammatory cytokines have the effect at the site of injury of increasing the release of antibodies and their compliments, T and B cell activation, the adhesion of platelets to blood vessel walls, and extravascuarization of lymphocytes and macrophages. These changes lead to a localized environment at the site of injury including fever, tissue injury, tumor necrosis, induction of other cytokines and immunoregulation and apoptosis. This localized response is toxic not only to the source of the challenge to the host but also to the host cells within the penumbra of the proinflammatory cytokine response. Thus, it is not surprising that on a systemic level, such as may occur during overwhelming infection or serious trauma to the host, many of these proinflammatory cytokines are harmful to the host producing fever, inflammation, tissue destruction, and, in some cases, shock and death.

Representative of the action of the various proinflammatory cytokines is TNF. TNF is a proinflammatory cytokine produced by many cell types, including macrophages, monocytes, lymphoid cells and fibroblasts in response to inflammation, infection, and other environmental challenges. TNF elicits a wide spectrum of cellular responses, including fever, shock, tissue injury, tumor necrosis, anorexia, induction of other cytokines and immunoregulatory molecules, cell proliferation, differentiation and apoptosis. When released TNF has an effect at the site of injury of increasing the release of antibodies and their compliments, T and B cell activation, the adhesion of platelets to blood vessel walls, and extravascuarization of lymphocytes and macrophages. Systemically, TNF acts upon the hypothalamus and liver. TNF stimulates the hypothalamus to release corticotropin releasing hormone, suppress appetite and induce fever. In response to TNF, the liver initiates an acute phase response resulting in the synthesis of several proteins including C-reactive protein, coagulation factors and compliment factors. Also, TNF induces insulin resistance. In the defined area of injury or infection, TNF is vital to removing the particular infectious agent and adapting the body's immune response to the particular injury.

On a systemic level, however, in which TNF as well as other proinflammatory cytokines may be present at higher concentrations or for prolonged times, TNF can have deleterious effects on the body. At high concentrations TNF activates an IL-1 & Il-6 cascade that results in cachexia (wasting). Additionally, TNF can lead to systemic edema, hypoproteinemia, and neutropenia which can result in disseminated extravascular coagulation and eventually multiple organ failure. In chronic diseases such as cancer, TNF can also interfere with vital endogenous functions within the host. For example, TNF may interfere with the ability of endogenous erythropoietin to maintain the hematocrit of the host, leading to a condition referred to as the anemia of chronic diseases (ACD). A typical course of treatment with recombinant erythropoietin may not counteract the effects of the proinflammatory cytokine, thereby requiring the administration of elevated doses of recombinant erythropoietin just to maintain the normal hematocrit of the host. Beyond the additional costs associated with the increased dosing, there is also the risk of adverse side effects from the increased doses of erythropoietin such as thrombosis. In addition to the conditions detailed below, proinflammatory cytokines, including, but not limited to, TNF are associated with diseases such as chronic inflammation, bacterial septic shock, bacterial toxic shock, graft vs. host disease, and HIV infection and AIDS.

Sepsis

Sepsis is the body's response to any kind of infection, e.g. bacterial, viral, parasitic, or fungal. Sites of infection are typically the lungs, the urinary tract, the abdomen, and the pelvis. In some cases, however, the actual site of infection cannot be detected. Although sepsis was once thought to be a systemic inflammatory response, it is now recognized that sepsis also includes prothrombotic diathesis and impaired fibrinolysis.

Once sepsis commences, widespread inflammation and clotting occurs throughout the body. Whereas in a healthy body, immune modulators would be released to fight the infection and heal the body, in sepsis, an overabundance of immune, regulators is released. The release of proinflammatory cytokines such as TNF, interleukin-1, and interleukin-18 lead to the inflammation of endothelial linings, elevation of the core temperature, loss of appetite, and anemia. In addition, inflammation of the lining of blood vessels activates the blood clotting process. Because sepsis decreases the body's natural production of protein C, which regulates blood clotting and controls inflammation, the body's ability to break down the formed blood clots is suppressed. This suppression leads to clotting in vital organs, limbs, fingers, and toes, which, in turn, leads to organ failure or gangrene.

Sepsis may present itself in varying degrees. For example, in cases of severe sepsis, which occurs when acute organ dysfunction or failure results, the body's normal defense reaction goes into overdrive, setting off a cascade of events that can lead to widespread inflammation and blood clotting in tiny vessels throughout the body. Septic shock occurs when a patient with severe sepsis experiences cardiovascular system failure. This failure causes the blood pressure to drop, which, in turn, deprives vital organs of an adequate oxygenated blood supply. Septicemia is a sepsis that has an infection in the bloodstream itself. In fact, septicemia may cause ischemia, i.e., poor blood supply to at least one organ. For example, when blood flow to the kidneys is reduced to dangerously low levels for substantial time period, ischemic acute renal failure (ARF) may develop. The depressed blood flow also results in necrosis, or tissue death, in affected organs.

Providing the source of the sepsis can be identified, many cases of sepsis will respond to treatment. Once isolated, a treatment regime specific to the cause of infection is initiated. Known treatment includes the use of antibiotics, surgical excision of infected or necrotic tissues, drugs that increase activated protein, and steroids (in cases of septic shock). For example, a typical course of sepsis treatment includes administration of a broad spectrum antibiotic until the cause of infection is isolated. However, the mortality rate of sepsis patients remains relatively high in cases of sepsis where the cause and/or area of infection is not ascertainable.

Depending on the severity of sepsis, anti-infection agents, draining techniques, fluids, drugs to raise the mean arterial blood pressure (MAP) such as norepinephrine and phenylephrine, drugs to improve renal function such as dopamine, drugs to increase oxygen delivery and oxygen consumption such as dobutamine and epinephrine, mechanical ventilators to support breathing, and dialysis for kidney failure may be used in the course of treatment. In addition, pharmacological agents that have been shown to have beneficial effects on immune responses following shock and sepsis include ATP-$MgCl_2$, nonanticoagulant heparin, calcium channel blockers, chloroquine, cyclooxygenase inhibitors, PAF antagonists, anti-inflammatory cytokines, growth factors, dietary manipulation, anti-TNF antibodies, activated protein C (Xigris®, Eli Lilly, Indianapolis, Ind.), and sex hormones. Recovery from sepsis is greatest when the condition is quickly diagnosed and promptly treated.

Recombinant erythropoietin (rhu-EPO), commercially available under tradenames PROCRIT® (from Ortho Biotech Inc., Raritan, N.J.), EPOGEN® (from Amgen, Inc., Thousand Oaks, Calif.), and NEORECORMON (from Roche, Basel, Switzerland)has also recently been investigated with regard to treatment of various conditions related to sepsis. In addition, U.S. Patent Publication No. 2003/0083251 generally discloses the use of rhu-EPO to aid in the regeneration of renal tubular cells and prevention of apoptosis of the renal tubular cells in order to treat patients with ischemic ARF. Furthermore, US Patent Publication No. 2002/0061849 generally discloses the use of rhu-EPO to aid in the treatment of inflammation in a non-ischemic condition in one or more organs. However, because of erythropoietin's erythropoietic effects—increased hematocrit, vasoconstriction, hyperactivation of platelets, pro-coagulant activity, and increased production of thrombocytes—treatment with rhu-EPO poses additional risks given the widespread clotting in vital organs, limbs, fingers, and toes that is associated with sepsis.

Adhesions.

In addition to sepsis, proinflammatory cytolines, such as TNF, have been associated with the formation of adhesions, abnormal fibrous bands or connections between organs and other structures of the body, as well. Adhesions may be a complication of, or related to, sepsis but also may occur independently. For example, adhesions may form as a result of surgery, trauma, infection, chemotherapy, and radiation. In fact, adhesions are almost an inevitable outcome of surgery, i.e., about 93 percent of patients who have undergone abdominal surgery suffer from adhesions to some degree (compared with adhesion formation in about 10.4 percent of patients who had never undergone a previous abdominal operation). See D. Menzies and H. Ellis, *Intestinal Obstruction from Adhesions—How Big is the Problem*?, ANN. R. COLL. SURG. ENGL. 72: 60-3 (1990).

The formation of adhesions can cause severe pain and apply unnatural pressure or tension on organs or other structures of a patient. For example, adhesions in the abdominal region of the body may cause the intestines of a patient to become trapped or squeezed between organs or other structures of the body. In some cases, the intestines may become blocked or significantly obstructed due to nearby adhesions.

The formation of these abnormal connections between two parts of a body leads to a host of other conditions. For example, as cesarean sections are becoming a more common method of childbirth, women who undergo this major abdominal surgery are likely to form adhesions and, as a result, experience chronic pelvic pain. In addition, adhesions involving female reproductive organs may lead to infertility and dyspareunia.

A number of agents have been researched in connection with preventing and treating adhesions, e.g., dextran, corticosteroids, phosphatidylcholine, phospholipase inhibitors, non-steroidal anti-inflammatory drugs, proteoglycans, heparin, and tissue plasminogen activator. See, e.g., C. L. Kowalczyk and M. P. Diamond, *The Management of Adhesive Disease*, in PERITONEAL ADHESIONS 315-324 (K. H. Treutner and V. Schumpelick, eds., 1997). Some, but not all of these agents, are believed to be effective in the treatment of adhesions because of their ability to interfere with coagulation and fibrinolysis. Clinical experience with the majority of these agents, however, is limited due to bleeding complications. In addition, hyaluronic acid derivatives have been shown to prevent postsurgical adhesions, particularly in the intra-abdominal area. See, e.g., J. M. Becker et al., *Prevention of Postoperative Abdominal Adhesions by a Sodium Hyaluronate-based Bioresorbable Membrane: A Prospective, Randomized, Double-blind Multicenter Study*, in J. AM. COLL. SURG. 183 297-306 (1996). Furthermore, beta-glucan, which is a glucose polymer that binds with high affinity to the receptors on monocytes and neutrophils in a competitive manner, has been shown to have a reducing effect on the frequency of adhesion after experimentally developed intraabdominal sepsis in Wistar rats. A. Bedirli et al., *Prevention of Intraperitoneal Adhesion Formation Using Beta-Glucan After Ileocolic Anastomosis in a Rat Bacterial Peritonitis Model*, in AM. J. SURG. 185 339-343 (2003).

Surgery may also be used as a course of treatment for adhesions. Generally, a physician will perform surgery to sever the adhesions from the organ or other part of the body. Given that adhesions are often a complication of surgery, however, surgery to remove adhesions frequently results in the formation of new adhesions. While some surgical procedures involve placement of sleeves over organs adjacent to the areas affected by the surgery and thus, help to prevent adhesions involving these organs, such procedures have had mixed results. In addition, the organ sleeves also require additional surgery to remove the sleeves.

Thus, despite the increased awareness with regard to adhesions, research into treatment methods have met with limited success. Many physicians are unwilling or unable to address the treatment of adhesions and many insurance companies are unwilling to pay for treatments that are, at best, marginally successful.

Wound Healing.

Healing is an essential process of the body that reestablishes the integrity of damaged tissue. This process is often viewed in terms of wounds, ulcers or lesions of the skin resulting from various causes such as trauma, surgery, pressure (bed sores), bums, diabetes, etc. The severity of the wounds is characterized by the extent the wound penetrates the skin. Stage I wounds are characterized by redness or discoloration, warmth, and swelling or hardness. Stage II wounds, partial thickness wounds, penetrate the epidermis and superficial dermis of the skin. Stage III wounds, fall thickness wounds, penetrate through the dermis of the skin but do not penetrate the membrane separating the skin from deeper organs. Stage IV wounds involve damage to the underlying muscle or bone.

Although all wounds heal through the same process: inflammation, epithelialization, angiogenesis, and the accumulation of matrix; the ease with which the wound heals is largely based on the severity of the wound and the health of the wounded individual. In general, Stage I and Stage II wounds heal through the regeneration of epithelial cells by the underlying dermis. Whereas, Stage III and IV wounds heal through the production of a scar. Proinflammatory cytokines, such as TNF, play a role in the healing of wounds, however, it is speculated that TNF may have an adverse effect on the accumulation of collagen in the healing wound and ultimately on the time the wound takes to heal and the strength of the repaired tissue.

Several therapeutics as well as therapeutic methods have been developed to assist the body in healing wounds. Several compounds are considered to have a therapeutic effect on wound healing including, but not limited to, growth factors (epidermal growth factor, Insulin-like Growth Factor, human growth hormone, fibroblast growth factor, vascular endothelial growth factor, interleukin-6, and interleukin-10), nutritional supplements (arginine, glutamine, vitamin C, vitamin B5, Bromelain, Curcumin, zinc, copper), and herbal supplements (aloe vera, Centella). Furthermore, various therapeutic methods including, but not limited to, hyperbaric oxygen therapy, whirlpool therapy, ultrasound therapy, electrical stimulation, and magnetic therapy have been utilized to aid the body in healing wounds.

If a wound does not heal properly or fails to heal at all it can lead to several complications chief among them scarring and infection. Depending upon the severity of the wound, the body may generate scar tissue in healing the wound. Aside from the aesthetic concerns of a scar, the scar may impair movement of the individual depending upon its severity. Additionally, a wound presents an opportunity for bacteria and other infectious agents to enter the body. Depending upon the severity of infection it may spread and become systemic leading to sepsis or septicemia.

Rhu-EPO has also been investigated for its possible healing effects in rat models of random ischemic flaps. For example, rhu-EPO has been shown to reduce necrosis, decrease neutrophil infiltration, and prevent increased temperature with regard to ischemic skin flap injuries. See M. Buemi et al., *Recombinant Human Erythropoitein Influences Revsacularization and Healing in a Rat Model of Random Ischaemic Flaps*, ACTA DERM VENERBOL, 82: 411-417 (2002). This finding suggests that rhu-EPO administration can improve the wound healing process, both in early and late stages of injury, by reducing the inflammatory response, increasing the density of capillaries in ischemic flaps and allowing earlier repair of a damaged area. However, as mentioned above, because rhu-EPO has erthyropoictic activity, the use of rhu-EPO for treatment of these conditions may cause a greater degree of clotting or complications than already initiated by the healing process.

In sum, no one agent or treatment strategy has demonstrated sufficient value for the management of sepsis cases, the incidence of sepsis, the formation of adhesions, wound healing or general inflammatory conditions. In fact, the mortality associated with sepsis and related conditions remains high. Every year, approximately 215,000 people die from severe sepsis and one out of every three patients who develop severe sepsis will die within a month. And, cases of sepsis are expected to rise in the future due to the increased awareness of the condition and sensitivity for the diagnosis, the number of immunocomprorrised patients, the use of invasive procedures, the number of resistant microorganisms, and the growth of the elderly population. In addition, the chronic pain associated with adhesions and general inflammatory conditions is often untreated due to the lack of a successful treatment strategy.

Thus, there exists a need in the art for method and therapeutics for treating, preventing, delaying the onset of, and reducing the effects of proinflammatory cytokines for the purposes of limiting the penumbra of their action and further addressing their systemic effect. In particular, a need exists for treating, preventing, delying the onset of, and reducing the effects of proinflammatory cytokines in conditions of sepsis, adhesions, wounds, chronic disease and general inflammatory conditions. In addition, it would be beneficial to provide methodoligies that have the ability to repair or prevent damage to tissue in ischemic conditions.

SUMMARY OF THE INVENTION

The present invention is directed to a method of treating, preventing, delaying the onset, and/or reducing the effects of sepsis, adhesions, general inflammatory conditions, and combinations thereof by administering at least one tissue protective cytokine in a therapeutically effective amount. In addition, the present invention relates to the prevention or reduction of scarring relating to injury and incisions using at least one tissue protective cytokine. The at least one tissue protective cytokine may be any tissue protective cytokine having tissue protective functionality. In one embodiment, however, the at least one tissue protective cytokine is a chemically modified EPO. In another embodiment, the chemically modified EPO is carbamylated EPO.

One embodiment of the present invention relates to a method of treating, preventing, delaying the onset of, or reducing the effects of proinflammatory cytokines in a mammal. Other embodiments relate to methods of treating, preventing, delaying the onset of a condition associated with an effect of proinflammatory cytokines. Some examples of conditions associated with the effects of proinflammatory cytokines include sepsis, adhesions, wounds, inflammation or chronic disease. These methods may involve the steps of administering a therapeutically effective amount of one or more tissue protective cytokines in a pharmaceutical carrier.

In addition, the present invention also is directed to pharmaceutical compositions that may be used in the methods described herein. For instance, one embodiment is directed toward a pharmaceutical composition comprising an amount of at least one tissue protective cytoline effective in treating, preventing, delaying the onset of, or reducing the effects of proinflammatory cytokines in a mammal. Another embodiment is directed toward a pharmaceutical composition comprised of an amount of at least one tissue protective cytokine effective in treating, preventing, delaying the onset of a condition associated with proinflammatory cytokines in a mammal.

Some tissue protective cytokines used in the present invention may be chemically modified erythropoietin or mutated erythropoietin.

In some embodiments where a chemically modified erythropoietin is used, the chemically modified erythropoietin may include one or more of the following: i) an erythropoietin that lacks sialic acid moieties; ii) an erythropoietin having at least no sialic acid moieties; iii) an erythropoietin having at least no N-linked or no O-linked carbohydrates; iv) an erythropoietin having at least a reduced carbohydrate content by virtue of treatment of native erythropoietin with at least one glycosidase; v) an erythropoietin having at least one or more oxidized carbohydrates; vi) an erythropoietin having at least one or more oxidized carbohydrates and is chemically reduced; vii) an erythropoietin having at least one or more modified arginine residues; viii) an erythropoietin having at least one or more modified lysine residues or a modification of the N-terminal amino group of the erythropoietin molecule; ix) an erythropoietin having at least a modified tyrosine residue; x) an erythropoietin having at least a modified aspartic acid or a glutamic acid residue; xi) an erythropoietin having at least a modified tryptophan residue; xii) an erythropoietin having at least one amino group removed; xiii) an erythropoietin having at least an opening of at least one of the cystine linkages in the erythropoietin molecule; or xiv) a truncated erythropoietin. In another embodiment, the chemically modified erythropoietin lacks erythropoietin's erythropoietic effects. The chemically modified erythropoietin also may comprise carbamylated erythropoietin.

Similarly, in some embodiments involving a mutated erythropoietin, the mutated erythropoietin may be selected from one or more of the following mutations C7S, R10I, V11S, L12A, E13A, R14A, R14B, R14E, R14Q, Y15A, Y15F, Y15I, K20A, K20E, E21A, C29S, C29Y, C33S, C33Y, P42N, T44I, K45A, K45D, V46A, N47A, F48A, F48I, Y49A, Y49S, W51F, W51N, Q59N, E62T, L67S, L70A, D96R, K97D, S100R, S100E, S100A, S100T, G100A, G101I, L102A, R103A, S104A, S104I, L105A, T106A, T106I, T107A, T107L, L108K, L108A, S126A, F142I, R143A, S146A, N147K, N147A, F148Y, L149A, R150A, G151A, K152A, L153A, L155A, A160S, I6A, C7A, B13A, N24K, A30N, H32T, N38K, N83K, P42A, D43A, K52A, K97A, K116A, T132A, I133A, T134A, K140A, F148A, R150B, G151A, K152W, K154A, G158A, C161A, or R162A. In another embodiment, the mutated erythropoietin lacks erythropoietint's erythropoietic effects.

Two examples of proinflammatory cytokines are Interleukin and TNF. One or more effects of the proinflammatory cytokine may include fever, wasting, lethargy, anemia, edema, ischemia, organ failure and insulin resistance. Additional features and advantages of the present invention are described in greater detail below.

BRIEF DESCRIPTION OF THE DRAWINGS

Further features and advantages of the invention can be ascertained from the following detailed description that is provided in connection with the drawing(s) described below.

DETAILED DESCRIPTION OF THE INVENTION

Figure 1:
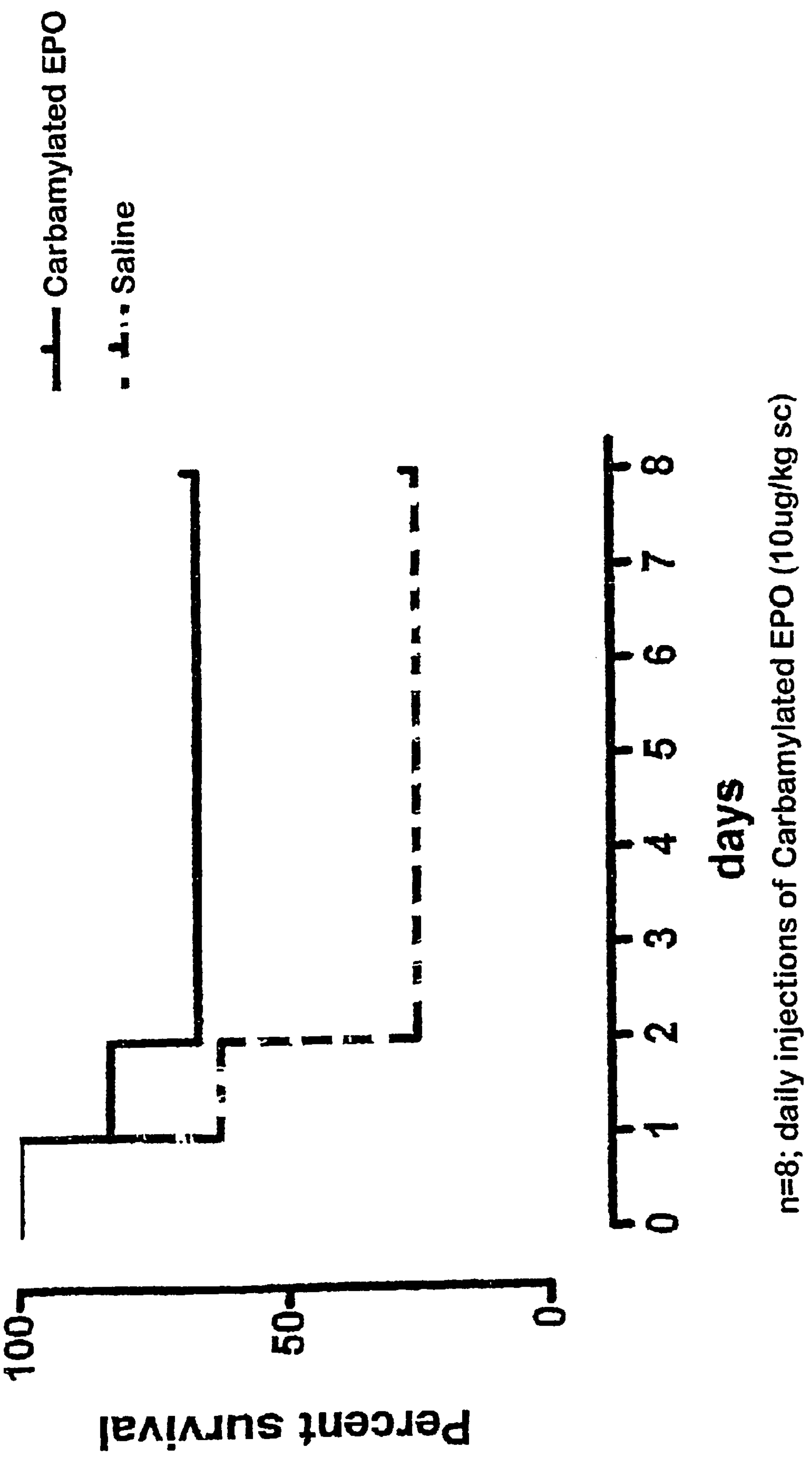
FIG. 1 is a graphical representation of the survival rate of Sprague Dawley rats after cecum ligation and puncture (CLP) and subsequent treatment with saline or a tissue protective cytokine of the invention.

The present invention is directed to novel compositions for the treatment, prevention, delay, or reduction of the effects of proinflammatory cytokines, such as TNF, in conditions including, but not limited to, sepsis and sepsis-related conditions, adhesions, wound healing, and chronic disease. The effects of the proinflammatory cytokines addressed by the tissue protective cytokines include, but are not limited to, fever, wasting, lethargy, anemia, edema, ischemia, organ failure and insulin resistance. The compositions of the invention are also contemplated for the treatment, prevention, delay, or reduction of the effects of inflammatory conditions in one or more organ(s) or tissue(s) resulting from infection, such as in the case of meningitis. In particular, the present invention is directed to compositions including tissue protective cytokines that are successful in the treatment of the effects of proinflammatory cytokines in conditions including sepsis, adhesions, wound healing, chronic disease, and inflammatory conditions.

In addition, the compositions of the inventions are useful in treating, preventing, and/or reducing the appearance of scarring from injury. For example, when a tissue protective cytokine of the present invention is used in conjunction with abdominal surgery, scarring may be substantially reduced. In one embodiment, the tissue protective cytokines of the present invention are used to prevent scarring from surgical incisions.

Compositions of the Invention

Any cytokine that exhibits tissue protective capability is contemplated for use with the present invention. The compositions of the invention may include erythropoietin. For example, a suitable tissue protective cytokine of the invention may be an EPO molecule, which may exist in a number of forms, e.g. $\alpha$, $\beta$, asialo and others. The $\alpha$ and $\beta$ forms have the same potency, biological activity, and molecular weight, but differ slightly in the carbohydrate components, while the asialo form is an $\alpha$ or $\beta$ form with the terminal sialic acids removed from the carbohydrate components.

Also, any tissue protective cytokine capable of treating, preventing, delaying the onset of, and/or reducing the effect of sepsis, sepsis-related conditions, and general inflammatory conditions is contemplated as well. As used herein, the term "tissue protective cytokines" refer to any cytokine that is a derivative of erythropoietin that possesses the tissue protective activity of erythropoietin. Preferably the tissue protective cytokine lacks at least one or more of erythropoietin's erythropoietic effects. Most preferably, the tissue protective cytokine lacks all of the erthropoietic effects of erythropoietin. For example, this may be accomplished by modifying erythropoietin through chemical or mutational processes that affect its pharmacological attributes (reduction in half-life) or structural ability to bind to the erythropoietin receptor homodimer. Non-limiting examples of suitable tissue protective cytokines for use with the present invention include the tissue protective cytokines disclosed in International Publication No. WO/02053580 and U.S. Patent Publication Nos. 2002/0086816 and 2003/0072737, which are incorporated by reference herein in their entirety.

In addition, the tissue protective cytokines for use with the present invention may include EPO molecules with a modification of at least one arginine, lysine, tyrosine, tryptophan, or cysteine residue or carboxyl groups are also contemplated for use as tissue protective cytokines according to the present invention. These residues may be chemically modified by guanidination, amidination, carbamylation, trinitrophenylation, acylation (acetylation or succinylation), nitration, or mixtures thereof, as disclosed in International Publication No. WO/02053580.

Thus, the tissue protective cytokine of the present invention may be carbamylated EPO. As discussed in the background of the invention, rhu-EPO has been researched in connection with treatment of acute renal failure, which is a possible complication of septicemia. However, because rhu-EPO has erythropoietic activity, i.e., the ability to maintain hematocrit levels in the body and hyperactivation of platelets, red blood cells are increased and platelets become hyperactive upon administration thereof resulting in the blood thickening and an increased risk of thrombosis. Thus, the use of rhu-EPO would likely exacerbate the widespread clotting that occurs as a result of sepsis.

Unlike rhu-EPO and selected other modified EPO molecules, carbamylated EPO does not retain erythropoietic activity and fails to bind with the classic homodimer erythropoietin receptor as is noted in PCT application No. PCT/US04/013099, filed Apr. 26, 2004, hereby incorporated in its entirety. Carbamylated EPO, however, does advantageously maintain the tissue protective functionality of endogenous EPO. It is believed that the retained tissue protective function of carbamylated EPO is mediated through its interaction with a tissue protective receptor complex as disclosed in PCT application No. PCT/US04/013099. Thus, carbamylated EPO may be used to treat, prevent, delay the onset, and/or reduce the effects of pro-inflammatory cytokines such as TNF within conditions including, but not limited to, sepsis, adhesions, wound healing, chronic diseases and general inflammatory conditions without posing the risk of further clotting associated with the administration of erythropoietin. In addition, because the carbamylated EPO molecules of the present invention are effective in protecting against necrosis, the carbamylated EPO molecules of the present invention are particularly beneficial in treating, preventing, delaying the onset, and/or reducing the effects of sepsis, adhesions, and general inflammatory conditions in patients susceptible to stroke, myocardial infarction, deterioration of mental faculties, and age-related conditions.

Therefore, the tissue protective cytokine of the invention may be a modified EPO with alteration of at least one or more lysine residues or the N-terminal group of the EPO molecule, which for purposes of this application, may also be referred to as "sites". The modifications may result from the reaction of the lysine residue or N-terminal amino group with an amino-group modifying agent. For example, the generic reaction scheme below is representative of one method to carbamylate proteins, such as EPO:

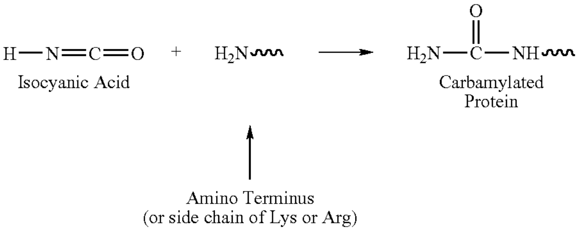

In another embodiment, one or more lysine residues on an EPO molecule may be carbamylated by virtue of reaction with a cyanate ion. For example, one or more lysine residues may be modified by incubation with 4-sulfophenylisothiocyanate. In yet another embodiment, one or more lysine residues on the EPO molecule are alkyl-carbamylated, aryl-carbamylated, or aryl-thiocarbamylated with an alkyl isocyanate, an aryl isocyanate, or an aryl-thioisocyanate, respectively. In still another embodiment, one or more lysine residues are akylated by a reactive alkylcarboxylic or arylcarboxylic acid derivative, e.g., acetic anhydride, succinic anhydride, or phthalic anhydride. The modified lysine residue may also be chemically reduced.

One or more lysine residues may also be carbamylated by reacting the residue(s) with trinitrobenzenesulfonic acid, or a salt thereof. In yet another embodiment, one or more lysine residues may be modified by reaction with a glyoxal or a glyoxal derivative, e.g., methylglyoxal ir 3-deoxyglucosone, to form the corresponding alpha-carboxyalkyl derivatives.

Other methods of carbamylation may be used in accordance with the present invention. For example, the method disclosed in Plapp et al., J. Biol. Chem., 246: 939-945 (1971) is a suitable way of making the carbamylated EPO according to the present invention. Another example of a method of carbamylation is discussed in Satake et al, 1990, *Biochim. Biophys. Acta* 1038:125-9, where six of the lysine residues in erythropoietin were carbamylated.

And, as mentioned above, any of the forms of EPO may be used according to the present invention. Thus, as an example: in one embodiment, the EPO molecule subject to carbamylation is in α form; in another embodiment, the EPO molecule subject to carbamylation is in β form; and in yet another embodiment, the EPO molecule subject to carbamylation is asialic.

The carbamylation process preferably occurs for a period of time sufficient to substantively reduce or completely eliminate erythropoietic activity. In one embodiment, the carbamylation process is performed for a sufficient time period to remove at least about 90 percent of the sites. In another embodiment, the carbamylation process is performed for a sufficient time period to remove at least about 95 percent of the sites. In still another embodiment, the carbamylation process is performed for a sufficient time period to remove 100 percent of the sites. Alternatively, this may be viewed as carbamylating erythropoietin for a period of time sufficient to carbamylate at least six lysine residues in one embodiment, at least seven lysines in another embodiment, and at least eight lysine residues in another embodiment. The time required for sufficient carbamylation to occur may vary. For instance, sufficient carbamylation may occur over a period up to about 6 to 24 hours, up to about 10 to 20 hours, or up to about 16 hours.

The tissue protective cytokines for use with the present invention may also be obtained by limited proteolysis, removal of amino groups, and/or mutational substitution of arginine, lysine, tyrosine, tryptophan, or cysteine residues by molecular biological techniques as disclosed in Satake et al, 1990, Biochem. Biophys. Acta 1038:125-9, which is incorporated by reference herein in its entirety. For example, suitable tissue protective cytokines include at least one or more mutated EPOs having a site mutation at C7S, R10I, V11S, L12A, E13A, R14A, R14B, R14E, R14Q, Y15A, Y15F, Y15I, K20A, K20E, E21A, C29S, C29Y, C33S, C33Y, P42N, T44I, K45A, K45D, V46A, N47A, F48A, F48I, Y49A, Y49S, W51F, W51N, Q59N, E62T, L67S, L70A, D96R, K97D, S100R, S100E, S100A, S100T, G101A, G101I, L102A, R103A, S104A, S104I, L105A, T106A, T106I, T107A, T107L, L108K, L108A, S126A, F142I, R143A, S146A, N147K, N147A, F148Y, L149A, R105A, G151A, K152A, L153A, L155A, A160S, I6A, C7A, B13A, N24K, A30N, H32T, N38K, N83K, P42A, D43A, K52A, K97A, K116A, T132A, I133A, T134A, K104A, F148A, R150B, G151A, K152W, K154A, G158A, C161A, and/or R162A. Examples of the above-referenced modifications are described in co-pending U.S. Patent Publication Nos. 2003/0 104988, 2002/0086816 and 2003/0072737, which are incorporated by reference herein in their entirety. In the mutein nomenclature used herein, the changed amino acid is depicted with the native amino acid's one letter code first, followed by its position in the EPO molecule, followed by the replacement amino acid one letter code. For example, S100E refers to a human EPO molecule in which, at amino acid 100, the serine has been changed to a glutamic acid In another embodiment, the tissue protective cytokine may include one or more of the above site mutations, providing that the site mutations do not include I6A, C7A, K20A, P42A, D43A, K45D, K45A, F48A, Y49A, K52A, K49A, S100B, R103A, K116A, T132A, I133A, K140A, N147K, N147A, R150A, R150E, G151A, K152A, K154A, G158A, C161A, or R162A.

In still another embodiment, the tissue protective cytokines may include combinations of site mutations, such as K45D/S100E, K97D/S100E, A30N/H32T, K45D/R150E, R103E/L108S, K140A/K52A, K140A/K52A/K45A, K97A/K152A, K97A/K152A/K45A, K97A/K152A/K45A/K52A, K97A/K152A/K45A/K52A/K140A, K97A/K152A/K45A/K52A/K140A/K154A, N24K/N38K/N83K, and N24K/Y15A. In yet another embodiment, the tissue protective cytokines do not include any of the above combinations. In another embodiment, the tissue protective cytokines may include any of the above-referenced site mutations providing that the site mutations do not include any of the following combinations of substitutions: N24K/N38K/N83K and/or A30N/H32T.

Certain modifications or combinations of modifications may affect the flexibility of the mutein's ability to bind with its receptor, such as an EPO receptor or secondary receptor. Examples of such modifications or combinations of modifications include, but are not limited to, K152W, R14A/Y15A, I6A, C7A, D43A, P42A, F48A, Y49A, T132A, I133A, T134A, N147A, F148A, R150A, G151A, G158A, C161A, and R162A. Corresponding mutations are known to those of ordinary skill in the art to be detrimental in human growth hormone. Thus, in one embodiment, the tissue protective cytokine does not include one or more of the modifications or combinations of modifications that may affect the flexibility of the mutein's ability to bind with its receptor. Further discussion of such tissue protective cytokines is included in co-pending U.S. patent application Ser. No. 10/612,665, filed Jul. 1, 2003, entitled "Recombinant Tissue Protective Cytokines and Encoding Nucleic Acids Thereof for Protection, Restoration, and Enhancement of Responsive Cells, Tissues, and Organs," the entire disclosure of which is incorporated by reference herein.

Moreover, suitable tissue protective cytokines for use with the present invention includes the long acting chemically modified EPO molecules disclosed in International Application No. US03/028073, filed on Sep. 9, 2003, entitled "Long Acting Erythropoietins that Maintain Tissue Protective Activity of Endogeneous Erythropoietin", which is incorporated in its entirety by reference herein. For example, suitable tissue protective cytokines for use with the present invention includes EPO that has undergone at least one chemical modification to at least one of the N-linked oligosaccharide chains or the O-linked oligosaccharide chain, wherein the chemical modification includes oxidation, sulfation, phosphorylation, PEGylation, or a combination thereof. In one embodiment, the EPO molecule subject to chemical modification is in α form. In another embodiment, the EPO molecule subject to chemical modification is in β form. In yet another embodiment, the EPO molecule subject to chemical modification is asialic. In yet another embodiment, the EPO molecule subject to chemical modification may be ARANESP (Amgen, Thousand Oaks, Calif.) or CERA (Hoffmann-La Roche Inc., Nutley, N.J.).

A variety of host-expression vector systems may be utilized to produce the tissue protective cytokines of the present invention. For example, when the tissue protective cytokine is based on an EPO molecule, various host-expression systems may be used. Such host-expression systems represent vehicles by which EPO may be produced and subsequently purified, but also represent cells that may, when transformed or transfected with the appropriate nucleotide coding sequences, exhibit the modified erythropoietin gene product in situ. These include but are not limited to, bacteria, insect, plant, mammalian, including human host systems, such as, but not limited to, insect cell systems infected with recombinant virus expression vectors (e.g., baculovirus) containing EPO coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing erythropoietin-related molecule coding sequences; or mammalian cell systems, including human cell systems, e.g., HT1080, COS, CHO, BHK, 293, 3T3, harboring recombinant expression constructs containing promoters derived from the genome of mammalian cells, e.g., metallothionein promoter, or from mammalian viruses, e.g., the adenovirus late promoter; the vaccinia virus 7.5K promoter.

In addition, a host cell strain may be chosen that modulates the expression of the inserted sequences, or modifies and processes the gene product in the specific fashion desired. Such modifications and processing of protein products may be important for the function of the protein. As known to those of ordinary skill in the art, different host cells have specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells, including human host cells, include but are not limited to HT1080, CHO, VERO, BHK, HeLa, COS, MDCK, 293, 3T3, and WI38.

For long-term, high-yield production of recombinant proteins, stable expression is preferred. For example, cell lines that stably express the recombinant tissue protective cytokine-related molecule gene product may be engineered. Rather than using expression vectors that contain viral origins of replication, host cells can be transformed with DNA controlled by appropriate expression control elements, e.g., promoter, enhancer, sequences, transcription terminators, polyadenylation sites, and the like, and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method may advantageously be used to engineer cell lines that express the EPO mutein-related molecule gene product. Such engineered cell lines may be particularly useful in screening and evaluation of compounds that affect the functionality of the EPO-related molecule gene product.

Alternatively, the expression characteristic of an endogenous EPO mutein gene within a cell line or microorganism may be modified by inserting a heterologous DNA regulatory element into the genome of a stable cell line or cloned microorganism such that the inserted regulatory element is operatively linked with the endogenous erythropoietin mutein gene. For example, an endogenous EPO mutein gene that is normally "transcriptionally silent", i.e., an EPO gene that is normally not expressed, or is expressed only at very low levels in a cell line, may be activated by inserting a regulatory element that is capable of promoting the expression of an expressed gene product in that cell line or microorganism. Alternatively, a transcriptionally silent, endogenous EPO gene may be activated by insertion of a promiscuous regulatory element that works across cell types.

A heterologous regulatory element may be inserted into a stable cell line or cloned microorganism, such it is operatively linked with an endogenous erythropoietin gene, using techniques, such as targeted homologous recombination, which are well known to those of skill in the art, and also described French Patent No. 2646438, U.S. Pat. Nos. 4,215,051 and 5,578,461, and International Publication Nos. WO93/09222 and WO91/06667, the entire disclosures of which are incorporated by reference herein.

Pharmaceutical Compositions

The present invention also relates to pharmaceutical compositions including the tissue protective cytokines of the present invention. Because the tissue protective cytokines of the present invention advantageously have the ability to ameliorate the effects of proinflammatory cytokines, such as TNF, as well as the ability to protect tissues from cell death, the cytokines are contemplated for the treatment of sepsis, adhesions, wounds, chronic disease and inflammatory conditions in individuals also at risk for various tissue injuries, such as stroke and myocardial infarction.

In addition, the tissue protective cytokines of the present invention are contemplated for treatment of sepsis, adhesions, wounds and general inflammatory conditions in individuals also experiencing deterioration of mental faculties, such as Alzheimer's, Parkinson's and the like.

The pharmaceutical compositions of the invention contain a therapeutically effective amount of the tissue protective cytokine of the present invention, preferably in purified form. As used herein, the term "therapeutically effective amount" means an amount of tissue protective cytokine that is nontoxic but sufficient to provide the desired effect and performance at a reasonable benefit/risk ratio attending any medical treatment.

The formulation should suit the mode of administration. In other words, the pharmaceutical compositions of the invention include an amount of the tissue protective cytokine(s) of the invention such that the targeted effects of proinflammatory cytokines, i.e., fever, wasting, lethargy, anemia, edema, ischemia, organ failure, and insulin resistance, or conditions related to proinflammatory cytolines, i.e., sepsis, adhesions, wound healing, chronic disease or an inflammatory condition, is treatable provided the proper dose and strategy is employed. And, as discussed in more detail below, the pharmaceutical composition should be delivered in a non-toxic dosage amount.

In one embodiment, a chemically modified or mutated erythropoietin is included in the pharmaceutical composition of the invention. In another embodiment the chemically modified erythropoietin is a carbamylated EPO. The carbamylated EPO may be an EPO molecule with at least one or more modified lysine residues or a modified N-terminal group. In another embodiment, the mutated erythropoietin may be S100E. In addition, the present invention contemplates the use of a mixture of tissue protective cytokines produced by any of the methods of the present invention described above in the pharmaceutical compositions of the invention. For example, the pharmaceutical composition of the invention may include at least one carbamylated EPO that is a result of modifying one or more lysine residues and at least one mutated EPO that is the result of modifying an amino group within erythropoietin, such as S100E.

The pharmaceutical compositions of the invention may include a therapeutically effective amount of the tissue protective cytoline and a suitable amount of a pharmaceutically acceptable carrier so as to provide the form for proper administration to the patient. In a specific embodiment, the term "pharmaceutically acceptable" means approved by a regulatory agency of the Federal or a state government or listed in the U.S. Pharmacopeia or other generally recognized foreign pharmacopeia for use in animals, and more particularly in humans. The term "carrier" refers to a diluent, adjuvant, excipient, or vehicle with which the therapeutic is administered.

Such pharmaceutical carriers can be sterile liquids, such as saline solutions in water and oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The pharmaceutical compositions of the invention may also contain minor amounts of wetting or emulsifying agents, or pH buffering agents. These compositions can take the form of solutions, suspensions, emulsion, tablets, pills, capsules, powders, sustained-release formulations and the like.

The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Treatment and Administration Methods

Figure 6:
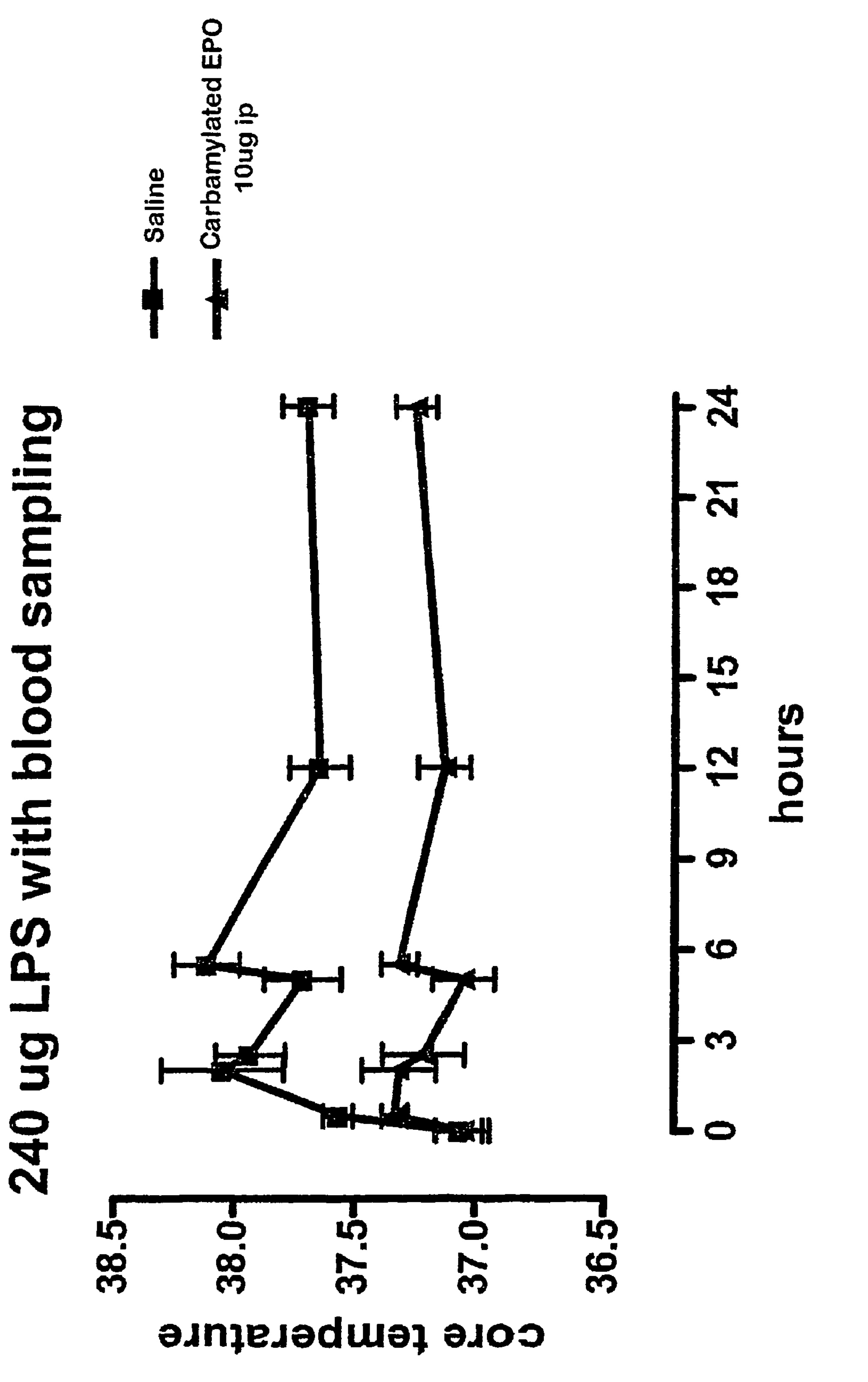
FIG. 6 is a chart demonstrating the core body temperature for Sprague Dawley rats treated with saline or a tissue protective cytokine after lippopolysaccharide (LPS) induced sepsis for a period of 24 hours.

The aforementioned tissue protective cytokines and pharmaceutical compositions including the tissue protective cytokines are intended for the therapeutic or prophylactic treatment, prevention, delay, and reduction of the effects of proinflammatory cytokines, such as TNF. These effects include fever, wasting, lethargy, anemia, edema, ischemia, organ failure and insulin resistance. For example, as demonstrated below in Example 4, the tissue protective cytokines of the present invention reduced the fever, elevation of the body's core temperature above the body's normal core temperature, associated with the release of proinflammatory cytokines. As is demonstrated in FIG. 6, the administration of a tissue protective cytokine, carbamylated erythropoietin, resulted in a greater than 50% reduction in the fever experienced as a result of subjecting a rat to LPS. The tissue protective cytokines may be administered to treat, prevent, delay or reduce conditions related to proinflammatory cytokines such as sepsis and sepsis-related conditions such as adhesions.

In addition, the tissue protective cytokines of the present invention are also contemplated for the treatment and prevention of inflammatory conditions in one or more organ(s) or tissue(s). The organs include, but are not limited to, the airways and lung, the kidney and urinary tract system, and the prostate. As used herein, the term "inflammatory condition" refers to a condition in which mechanisms such as the reaction of specific T lymphocytes or antibody with antigen causes the recruitment of inflammatory cells and endogenous mediator chemicals. In some cases, the normal function of the organ or tissue will be altered by an increase in vascular permeability and/or by contraction of visceral smooth muscle.

Thus, the tissue protective cytokines of the present invention may be used to treat and/or prevent inflammatory conditions wherein the normal function of the organ(s) or tissue(s) is altered. These conditions may include ischemia-related conditions, as well as non-ischemia-related conditions, such as allergy, rheumatic diseases, and infection including viral, fungal, and bacterial infection. Furthermore, the injury or infection may be acute or chronic. In one embodiment, the tissue protective cytokines of the invention are contemplated for use in treating and/or preventing inflammatory conditions under non-ischemia conditions, i.e., conditions where there is a substantially normal blood supply to the organ(s) and/or tissue(s) in question.

Furthermore, the tissue protective cytokines of the present invention may be used to enhance the healing of wounds. This may be accomplished by reducing the time needed to heal, reducing the appearance of or completely eliminate scarring, reducing the risk of complications, or otherwise improving the quality of healing. For example, scarring from an incision may be dramatically reduced, if not completely avoided, when the tissue protective cytokines of the present invention are employed prior to, during, or after the incision occurs. In addition to surgical procedures the tissue protective cytokines of the present invention are useful in addressing wounds resulting from conditions including but not limited to trauma (blunt force and cuts), pressure (bed sores), burns, and diseases, such as diabetes or vascular insufficiencies.

Figure 7A:
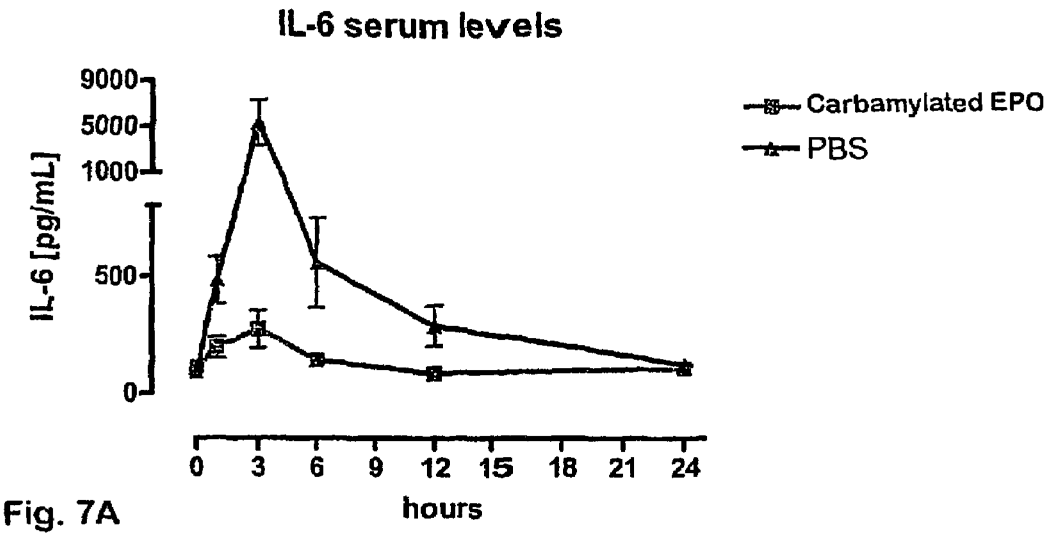
FIGS. 7(*a*) and (*b*) are charts demonstrating the levels of IL-6 (FIG. 7*a*) or TNF (FIG. 7*b*) in the serum of Sprague Dawley rats treated with saline or a tissue protective cytoline after LPS induced sepsis.
Figure 7B:
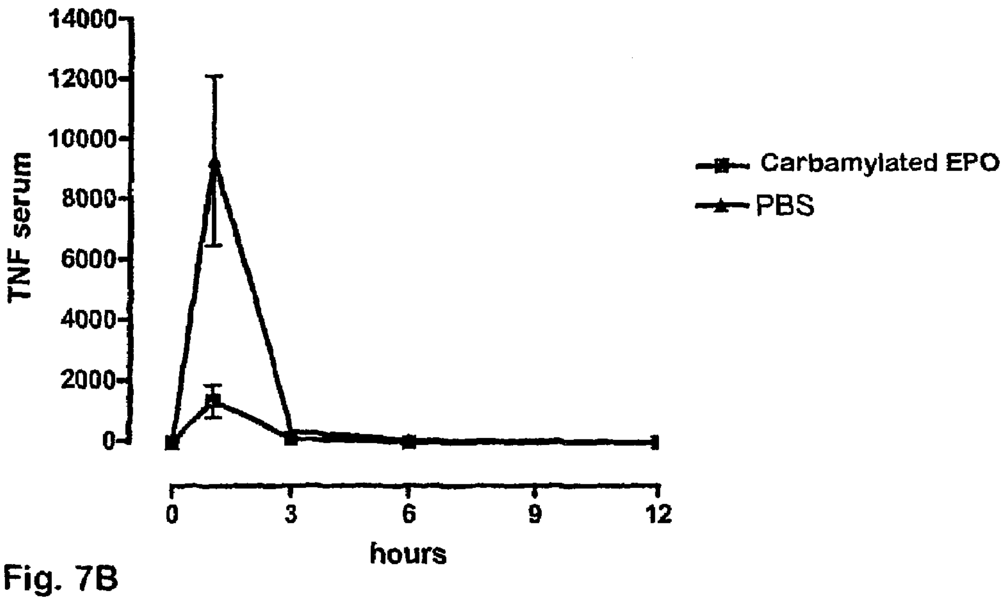

Moreover, the tissue protective cytokines and pharmaceutical compositions of the present invention may be used to address the effects of proinflammatory cytokines, such as TNF. As demonstrated in FIGS. 7*a* and 7*b*, the tissue protective cytokines of the present invention can reduce the upregulation of proinflammatory cytokines, IL-6 and TNF respectively, in response to an injury or infective agent. The tissue protective cytokines of the present invention may be administered in therapeutic doses to treat, prevent, reduce, or eliminate effects of proinflamrnmatory cytokines such as fever, wasting, lethargy, anermia, edema, ischemia, organ failure and insulin resistance. Given that the tissue protective cytokines interfere with the upregulation of proinflammatory cytokines, the tissue protective cytokines of the present invention may be able to restore endogenous functions interrupted by the proinflammatory cytokines without directly affecting those endogenous functions. Additionally, the tissue protective cytokines of the present invention may be administered in conjunction with other known therapeutic treatments for conditions related to proinflammatory cytokines to provide a synergistic effect. For example, a treatment for the anemia associated with cancer or other chronic diseases may involve the administration of a typical therapeutic dose of recombinant erythropoietin to restore the patient's hematocrit and a therapeutic dose of the tissue protective cytokines of the present invention to counteract the effects of proinflammatory cytokines. This would permit the use of lower doses of recombinant erythropoietin in such chronic disease thereby greatly reducing the risk of thrombolic events.

The tissue protective cytokines of the present invention may be used for systematic or chronic administration, acute treatment, and/or intermittent administration. In one embodiment, the pharmaceutical compositions of the invention are administered chronically to protect or enhance the target cells, tissue or organ. In another embodiment, the pharmaceutical compositions of the invention may be administered acutely, i.e., for a single treatment during injury. In yet another embodiment, the pharmaceutical compositions of the invention are administered in a cyclic nature.

The compositions of the invention may be administered prior to injury. As such, the tissue protective cytokines of the present invention may be administered prior to a surgical procedure to prevent sepsis, delay the onset of sepsis, and/or reduce complications from sepsis. For example, the tissue protective cytokines of the present invention may be given to a patient prior to abdominal surgery. And, as briefly mentioned above, administering the tissue protective cytokines of the present invention prior to surgery may not only have an effect with regard to sepsis, adhesions, and general inflammatory conditions, but they may also reduce the appearance of, or completely eliminate scarring from the surgery.

In addition, the compositions of the invention may be administered at the time of injury or shortly thereafter. Thus, a patient undergoing major abdominal surgery may be given the tissue protective cytokines of the present invention at the time of, or shortly thereafter, the surgical procedure in order to prevent, delay the onset of, or reduce complications stemming from sepsis, adhesions, or general inflammatory conditions. The tissue protective cytokines of the present invention may also reduce the appearance of, or completely eliminate scarring from the surgery if administered during or after injury.

For example, the tissue protective cytokines of the present invention may be used for irrigation purposes, e.g., while cleaning the wound, a saline solution including the tissue protective cytokine of the present invention may be administered to treat, prevent, delay the onset of, or reduce complications stemming from sepsis, adhesions, or general inflammatory conditions. Furthermore, the tissue protective cytokines of the present invention may be given to a pregnant woman following a cesarean section in order to prevent, delay the onset of, and/or reduce complications from sepsis, adhesions, and/or general inflammatory conditions. As another example, the tissue protective cytokines of the present invention may be given to a patient during chemotherapy to stave off sepsis, adhesions, or general inflammatory conditions.

In one embodiment, the tissue protective cytokines of the present invention are administered intravenously at the time of injury and subcutaneously for a predetermined period of time thereafter in order to prevent, delay the onset of, or reduce complications stemming from sepsis, adhesions, or general inflammatory conditions. For example, the compositions of the invention may be administered in an amount of about 10 μg/kg intravenously at the time of injury followed by 10 μg/kg subcutaneously for an allotted time.

In cases of a positive sepsis diagnosis, the compositions of the invention may be administered daily to treat sepsis, stabilize the patient, and prevent the sepsis condition from progressing to a more serious stage, e.g., severe sepsis or septic shock. In addition, the tissue protective cytokines of the present invention may be administered with known antibiotics, anti-fungals, anti-virals, and the like, including those listed within International Publication No. WO 2004/004656, hereby incorporated by reference in its entirety.

The administration of the composition may be parenteral, i.e., by a method other than the via the digestive tract. For example, parenteral administration may include intravenous injection, intraperitoneal injection, intra-arterial, intramuscular, intradermal, or subcutaneous administration. The composition may also be administered via inhalation or transinucosally, e.g., orally, nasally, rectally, intravaginally, sublingually, submucosally, and transdermally. In addition, the tissue protective cytolines of the present invention may be administered locally to the area in need of treatment, such as by the use of a perfusate; topical application, e.g., in conjunction with a wound dressing after surgery; by injection; by means of a catheter; by means of a suppository; or by means of an implant, said implant being of a porous, non-porous, or gelatinous material, including membranes, such as silastic membranes, or fibers. Combinations of the administration methods discussed above are contemplated by the present invention.

In one embodiment, the administration of the pharmaceutical composition of the invention is parenteral. Such administration may be performed in a dose amount of about 0.01 pg to about 5 mg, preferably about 1 pg to about 5 mg. In one embodiment, the dose amount is about 500 pg to about 5 mg. In another embodiment, the dose amount is about 1 ng to about 5 mg. In yet another embodiment, the dose amount is about 500 ng to about 5 mg. In still another embodiment, the dose amount is about 1 μg to about 5 mg. For example, the dose amount may be about 500 μg to about 5 mg. In another embodiment, the dose amount may be about 1 mg to about 5 mg. Such compositions may include aqueous and non-aqueous sterile injectable solutions or suspensions, which may contain antioxidants, buffers, bacteriostats and solutes that render the compositions substantially isotonic with the blood of an intended recipient. In this aspect of the invention, the pharmaceutical compositions may also include water, alcohols, polyols, glycerine, vegetable oils, and mixtures thereof.

Pharmaceutical compositions adapted for parenteral administration may be presented in unit-dose or multi-dose containers, for example sealed ampules and vials, and may be stored in a lyophilized (freeze-dried) condition requiring only the addition of a sterile liquid carrier, e.g., sterile saline solution for injections, immediately prior to use. Extemporaneous injection solutions and suspensions may be prepared from sterile powders, granules and tablets. In one embodiment, an autoinjector comprising an injectable solution of a long acting EPO of the invention may be provided for emergency use by ambulances, emergency rooms, and battlefield situations.

Intravenous Administration

In one embodiment, the pharmaceutical composition of the invention is formulated in accordance with routine procedures as a pharmaceutical composition adapted for intravenous administration to human beings. For example, the pharmaceutical composition may be in the form of a solution in sterile isotonic aqueous buffer. Where necessary, the pharmaceutical composition may also include a solubilizing agent and/or a local anesthetic such as lidocaine to ease pain at the site of the injection. The ingredients may be supplied either separately or mixed together in unit dosage form, for example, as a dry lyophilized powder or water-free concentrate in a hermetically-sealed container such as an ampule or sachette indicating the quantity of active agent. When the pharmaceutical compositions of the invention are to be administered by infusion, an infusion bottle with sterile pharmaceutical grade water or saline may be used for dispensing the composition. And, when the pharmaceutical composition are to be administered by injection, an ampule of sterile saline may be provided to mix the ingredients may be mixed prior to administration.

Oral Administration

One of ordinary skill in the art will recognize the pharmaceutical compositions of the present invention may be adapted for oral administration as capsules or tablets; powders or granules; solutions, syrups or suspensions (in aqueous or non-aqueous liquids); edible foams or whips; emulsions; or combinations thereof. The oral formulation may include about 10 percent to about 95 percent by weight active ingredient. In one embodiment, the active ingredient is included in the oral formulation in an amount of about 20 percent to about 80 percent by weight. In still another embodiment, the oral formulation includes about 25 percent to about 75 percent by weight of the active ingredient.

Tablets or hard gelatine capsules may include lactose, starch or derivatives thereof, magnesium stearate, sodium saccharine, cellulose, magnesium carbonate, stearic acid or salts thereof. Soft gelatine capsules may include vegetable oils, waxes, fats, semi-solid, liquid polyols, or mixtures thereof. Solutions and syrups may include water, polyols, sugars, or mixtures thereof.

Moreover, an active agent intended for oral administration may be coated with or admixed with a material that delays disintegration and/or absorption of the active agent in the gastrointestinal tract. For example, the active agent may admixed or coated with glyceryl monostearate, glyceryl distearate, or a combination thereof. Thus, the sustained release of an active agent may be achieved over many hours and, if necessary, the active agent can be protected from being degraded within the stomach. Pharmaceutical compositions for oral administration may also be formulated to facilitate release of an active agent at a particular gastrointestinal location due to specific pH or enzymatic conditions.

Transdermal Administration

Pharmaceutical compositions adapted for transdermal admimastration may be provided as discrete patches intended to remain in intimate contact with the epidermis of the recipient for a prolonged period of time. In addition, pharmaceutical compositions adapted for topical administration may be provided as ointments, creams, suspensions, lotions, powders, solutions, pastes, gels, sprays, aerosols, oils, eye drops, lozenges, pastilles, and mouthwashes and combinations thereof. When the topical administration is intended for the skin, mouth, eye, or other external tissues, a topical ointment or cream is preferably used. And, when formulated in an ointment, the active ingredient, i.e., the long acting EPO, may be employed with either a paraffinic or a water-miscible ointment base. Altematively, the active ingredient may be formulated in a cream with an oil-in-water base or a water-in-oil base. When the topical administration is in the form of eye drops, the pharmaceutical compositions of the invention preferably include the active ingredient, which is dissolved or suspended in a suitable carrier, e.g., in an aqueous solvent.

Nasal and Pulmonary Administration

Pharmaceutical compositions adapted for nasal and pulmonary administration may include solid carriers such as powders (preferably having a particle size of about 20 microns to about 500 microns). Powders may be administered by rapid inhalation through the nose from a container of powder held close to the nose. In an alternate embodiment, pharmaceutical compositions intended for nasal administration according to the present invention may include liquid carriers, e.g., nasal sprays or nasal drops. Preferably, the pharmaceutical compositions of the invention are administered into the nasal cavity directly.

Direct lung inhalation may be accomplished by deep inhalation through a mouthpiece into the oropharynx and other specially adapted devices including, but not limited to, pressurized aerosols, nebulizers or insufflators, which can be constructed so as to provide predetermined dosages of the active ingredient. Pharmaceutical compositions intended for lung inhalation may include aqueous or oil solutions of the active ingredient. Preferably, the pharmaceutical compositions of the invention are administered via deep inhalation directly into the oropharynx.

Rectal and Vaginal Administration

Pharmaceutical compositions adapted for rectal administration may be provided as suppositories or enemas. In one embodiment, the suppositories of the invention includes about 0.5 percent to 10 percent by weight of active ingredient. In another embodiment, the suppository includes about 1 percent to about 8 percent by weight active ingredient. In still another embodiment, the active ingredient is present in the suppository in an amount of about 2 percent to about 6 percent by weight. In this aspect of the invention, the pharmaceutical compositions of the invention may include traditional binders and carrier, such as triglycerides.

Pharmaceutical compositions adapted for vaginal administration may be provided as pessaries, tampons, creams, gels, pastes, foams or spray formulations.

Perfusion Administration

The pharmaceutical compositions of the invention may also be administered by use of a perfusate, i.e., pumping a liquid into an organ or tissue (especially by way of blood vessels). In such embodiments, the pharmaceutical composition preferably has about 0.01 pM to about 30 pM, preferably about 15 pM to about 30 nM, of the tissue protective cytokine of the present invention. In one embodiment, the perfusion solution is the University of Wisconsin (UW) solution (with a pH of about 7.4 to about 7.5 and an osmolality of about 320 mOSm/l), which contains about 1 U(10 ng)/ml to about 25 U(250 ng)/ml of an EPO compound of the present invention; 5 percent hydroxyethyl starch (preferably having a molecular weight from about 200,000 to about 300,000 and substantially free of ethylene glycol, ethylene chlorohydrin, sodium chloride, and acetone), 25 mM $KH_2PO_4$, 3 mM glutathione; 5 mM adenosine; 10 mM glucose; 10 mM HEPES buffer; 5 mM magnesium gluconate; 1.5 mM $CaCl_2$; 105 mM sodium gluconate; 200,000 units penicillin; 40 units insulin; 16 mg dexamethasone; and 12 mg phenol red. The UW solution is discussed in detail in U.S. Pat. No. 4,798,824, which is incorporated in its entirety by reference herein.

Local Administration

It may be desirable to administer the pharmaceutical compositions of the invention locally to the area in need of treatment. Such administration may be achieved by local infusion during surgery; topical application, e.g., in conjunction with a wound dressing after surgery; by injection; by means of a catheter; by means of a suppository; or by means of an implant, said implant being of a porous, non-porous, or gelatinous material, including membranes, such as silastic membranes, or fibers.

Controlled-Release Systems

In addition, as briefly discussed above with respect to transdermal administration, the tissue protective cytokines of the present invention may be delivered in a controlled-release system. For example, the tissue protective cytokine may be administered using intravenous infusion, an implantable osmotic pump, a transdermal patch, liposomes, or other modes of administration. Such controlled release systems may be placed in proximity of the therapeutic target, i.e., the target cells, tissue or organ, thus requiring only a fraction of the systemic dose.

Dosing

Selection of the preferred effective and non-toxic dose for the administration methods above will be determined by a skilled artisan based upon factors known to one of ordinary skill in the art. Examples of these factors include the particular form of tissue protective cytokine; the pharmacokinetic parameters of the tissue protective cytokine, such as bioavailability, metabolism, half-life, etc. (provided to the skilled artisan); the condition to be treated; the benefit to be achieved in a normal individual; the body mass of the patient; the method of administration; the frequency of administration, i.e., chronic, acute, intermittent; concomitant medications; and other factors well known to affect the efficacy of administered pharmaceutical agents. Thus the precise dosage should be decided according to the judgment of the practitioner and the circumstances of the particular patient.

Treatment Kits

The invention also provides a pharmaceutical pack or kit that include one or more containers filled with one or more of the ingredients of the pharmaceutical compositions of the invention. In one embodiment, the effective amount of the tissue protective cytokine and a pharmaceutically acceptable carrier may be packaged in a single dose vial or other container.

When the pharmaceutical composition of the invention is adapted for parenteral administration, for example, the composition may be stored in a lyophilized condition. Thus, the kit may include the lyophilized composition, a sterile liquid carrier, and a syringe for injections.

In one embodiment, the kit includes an ampule containing enough lyophilized material for several treatments such that the administrator would weigh out a specific amount of material and add a specific amount of carrier for each treatment session. In another embodiment the kit may contain a plurality of ampules each containing specific amounts of the lyophilized material and a plurality of containers each containing specific amounts of carrier, such that the administrator need only mix the contents of one ampule and one carrier container for each treatment session without measuring or weighing. In yet another embodiment, the kit contains an autoinjector including an injectable solution of the tissue protective cytokine(s) of the invention. In still another embodiment, the kit contains at least one ampule with the lyophilized composition, at least one container of carrier solution, at least one container with a local anesthetic, and at least one syringe (or the like). The ampules and containers are preferably hernetically-sealed.

When the pharmaceutical compositions of the invention are to be administered by infusion, the kit preferably includes at least one ampule with the pharmaceutical composition and at least one infusion bottle with sterile pharmaceutical grade water or saline.

A kit according to the present invention may also include at least one mouthpiece or specially adapted devices for direct lung inhalation such as pressurized aerosols, nebulizers, or insufflators. In this aspect of the invention, the kit may include the device for direct lung inhalation, which contains the pharmaceutical composition, or the device and at least one ampule of aqueous or oil solutions of the tissue protective cytokine(s) of the present invention.

When the tissue protective cytokine(s) of the invention is adapted for oral, transdermal, rectal, vaginal, or nasal, the kit preferably includes at least one ampule containing the active ingredient and at least one administration aid. Examples of administration aids include, but are not limited to, measuring spoons (for oral administration), sterile cleaning pads (for transdermal adminstration, and nasal aspirators (for nasal administration). Such kits may include a single dose of the tissue protective cytokine (acute treatment) or a plurality of doses (prolonged treatment).

In addition, the kit may be outfitted with one or more types of solutions. For example, the tissue protective cytokines of the invention may be made in an albumin solution and a polysorbate solution. If the kit includes the polysorbate solution, the words "Albumin free" preferably appear on the container labels as wells as the kit main panels.

Moreover, the kit may also include a notice in the form prescribed by a governmental agency regulating the manufacture, use or sale of pharmaceuticals or biological products, which notice reflects approval by the agency of manufacture, use or sale for human administration.

Assays to Determine Sepsis/Inflammation Treatability

The present invention also contemplates assays to determine whether a tissue protective cytokine is able to effectively treat, prevent, delay the onset of, or reduce complications of sepsis, adhesions, and inflammation resulting from infection. Any assay that includes laboratory controlled sepsis induction, adhesion induction, or inflammatory response induction is contemplated for the present invention.

For example, a suitable assay according to the invention may include a blind study where the cecum of Sprague Dawley rats are exposed and ligated just distally to the ileocecal valve to avoid intestinal obstruction. The cecum is then be punctured and squeezed gently to force out a small amount of feces, and then returned to the abdominal cavity. The release of feces into the organ induces infection which, in turn, induces sepsis, adhesions, inflammation, or a combination thereof. The abdomen is then sutured. The rats are preferably separated into groups with at least one group receiving saline and another group receiving the tissue protective cytokine to be tested. At the time of ligation, the various groups of animals are given a predetermined amount of saline or the tissue protective cytokine, preferably intraveneously. Subcutaneous administration of the selected treatment, i.e., saline or the tissue protective cytokine, may be undertaken for a predetermined time following the ligation procedure. In addition, the study may include a group of rats that have been opened, but not subjected to infection.

The animals may then be monitored for adhesions and illness scores. Table 1 provides a method of scoring an animal based on the formation of adhesions.

TABLE 1

| CUMULATIVE ADHESION SCORING SCALE | | |
|---|---|---|
| Points | 0 | No adhesions |
| | +1 | One adhesive band from the omentum to the target organ |
| | +1 | One adhesive band from the omentum to the scar |
| | +1 | One adhesive band from the omentum to the another place |
| | +1 | One adhesive band from adnexa/epididymal fat bodies to the target organ |
| | +1 | One adhesive band from adnexa/epididymal fat bodies to scar |
| | +1 | One adhesive band from adnexa/epididymal fat bodies to another place |
| | +1 | Any adhesive band other than described above (e.g., liver to scar) |
| | +1 | Target organ adherent to abdominal wall |
| | +1 | Target organ adherent to abdominal scar |
| | +1 | Target organ adherent to bowel |
| | +1 | Target organ adherent to liver or spleen |
| | +1 | Any other organ adherent |
| Total Score | | |

One point is given for each adhesion and a cumulative adhesion score is calculated. In one embodiment, the cumulative adhesion score is preferably 8 or less. In another embodiment, the cumulative adhesion score is about 5 or less. In still another embodiment, the cumulative adhesion score is about 3 or less.

An illness score may also be calculated for each animal based on a variety of factors. Factors used for this score include, but are not limited to, behavioral factors such as walking posture, rope hanging ability, investigatory behavior regarding surroundings, climbing foam pad up a wall, body responses such as erectness of hair, and oxygenation, and the number of adhesions formed. For example, when a rat is ill, the animal will hunch while walking and will not investigate his/her surroundings. In addition, the pulse rate of an ill rate is inaccurate, while a healthy rat typically has a pulse rate of about 300 beats/minute. Table 2 provides a method of scoring each animal with regard to illness in order to assess the effectiveness of the tissue protective cytokine being used for treatment

TABLE 2

| CUMULATIVE ILLNESS SCORE Behavioral Tests | |
|---|---|
| +1 | piloerection (hairs stand to erect) |
| +1 | immobility |
| +1 | Loss of Beam Balance |
| +1 | unable to hold or climb |
| +1 | Not using claws |
| +1 | Becoming hunchbacked |
| +1 | Abnormal walking |
| +1 | No exploration of surroundings |
| +1 | Not grasping a string within 30 seconds |
| +1 | reduced reflexes |
| +1 | Lack of appetite (food and drink) |
| +1 | Loss of body weight |
| +1 | moribund |
| +1 | Abnormal Heart Rate (< or > 50% normal) |

TABLE 2-continued

| CUMULATIVE ILLNESS SCORE<br>Behavioral Tests | |
|---|---|
| +1 | Spontaneous Hemorrhage |
| +1 | Decreased Oxygen Saturation |
| Total Score | |

On a continuum, a cumulative illness score of 14 or above signifies the death of the animal, while a much lower score indicates that the animal is relatively healthy. In one embodiment, a sepsis-induced animal has an illness score of about 5 or less after 8 days of treatment with at least one tissue protective cytokine of the invention. In another embodiment, an animal has an illness score of about 4 or less after treatment. In yet another embodiment, an animal has an illness score of about 2 or less after treatment. In still another embodiment, an animal has an illness score of about 1 or less after treatment.

EXAMPLES

The following non-limiting examples are merely illustrative of the preferred embodiments of the present invention, and are not to be construed as limiting the invention, the scope of which is defined by the appended claims. Parts are by weight unless otherwise indicated.

Example 1

Blind Study Using Rat Abdominal Sepsis Model

The cecum of Sprague Dawley rats was exposed, ligated just distally to the ileocecal valve to avoid intestinal obstruction, punctured twice with a 18-gauge needle, squeezed gently to force out a small amount of feces, and then returned to the abdominal cavity (feces introduced in peritoneum, which induced infection). The abdomen was closed with 3-0 silk sutures.

The animals were allocated to two groups:

Group 1: Sepsis induced, treated with saline (n=8). At time of ligation, animals in Group 1 were given 100 μl saline intraveneously. Daily subcutaneous saline administration (100 μl) followed for 8 days or until death.

Group 2: Sepsis induced, treated with carbamylated EPO (n=8). At time of ligation, animals were given 10 μg/kg carbamylated EPO (prepared so that erythropoietic activity is effectively eliminated) intraveneously in 100 μl of saline. Daily subcutaneous treatment followed for 8 days (or until death) at a dosage amount of 10 μg/kg in 100 μl saline.

Morbidity and Mortality

In Group 1, less than about 50 percent of the animals survived after 8 days. In Group 2, however, the survival rate was greater than about 50 percent, as illustrated graphically in FIG. 1. In particular, one day following the treatment there was about a 60 percent survival rate for animals in Group 1 compared to about a 80 percent survival rate for animals in Group 2. After 3 days, however, the survival rate of Group 1 dropped significantly to about 25 percent survival rate, whereas the survival rate of Group 2 animals was greater than about 60 percent. Thus, the animals receiving the carbamylated EPO of the present invention had a much higher survival rate than animals receiving saline.

Cumulative Adhesion Score

Specimens were taken from the peritoneal fluid and abscesses for aerobic and anaerobic culture. For aerobic culture, samples were incubated on blood on EMB agar for 24 hours at 37° C. For anaerobic culture, samples were layered on anaerobic blood agar and incubated in a Gas-Pak jar for 24 hours at 37° C. Growing colonies were identified with standard bacteriologic techniques.

Figure 2:
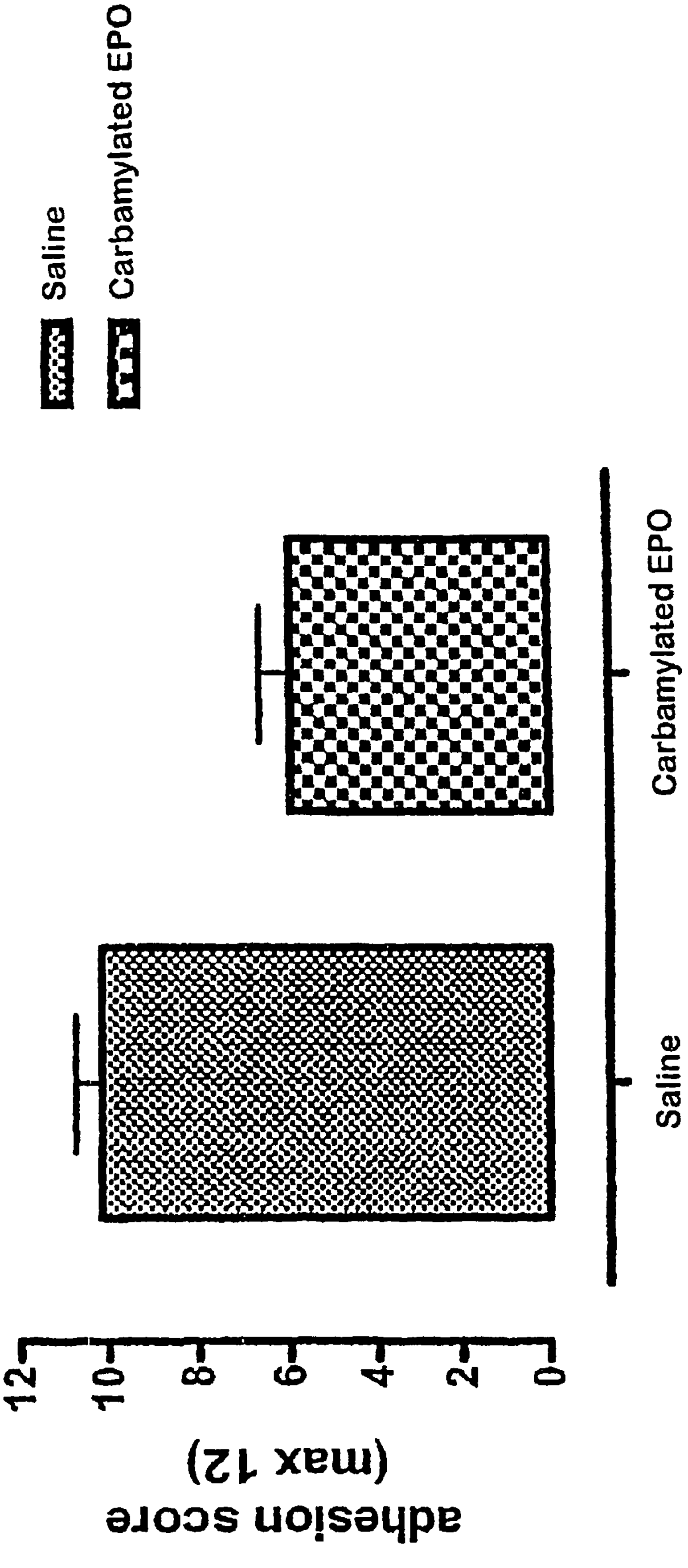
FIG. 2 is a graphical representation of the adhesion score for Sprague Dawley rats following CLP and subsequent treatment with saline or a tissue protective cytokine of the invention.

Dead animals were autopsied within 4 hours and the causes of death were recorded. Using Table 1 described earlier in the application, a cumulative adhesion score was calculated for each animal 24 hours post-injury and then averaged for the group (shown graphically in FIG. 2). In particular, the average total score of Group 1 was about 10, whereas the average total score of Group 2 was about 6. In sum, the animals receiving the carbamylated EPO of the present invention had less adhesions than animals receiving saline.

Illness Score

Figure 3:
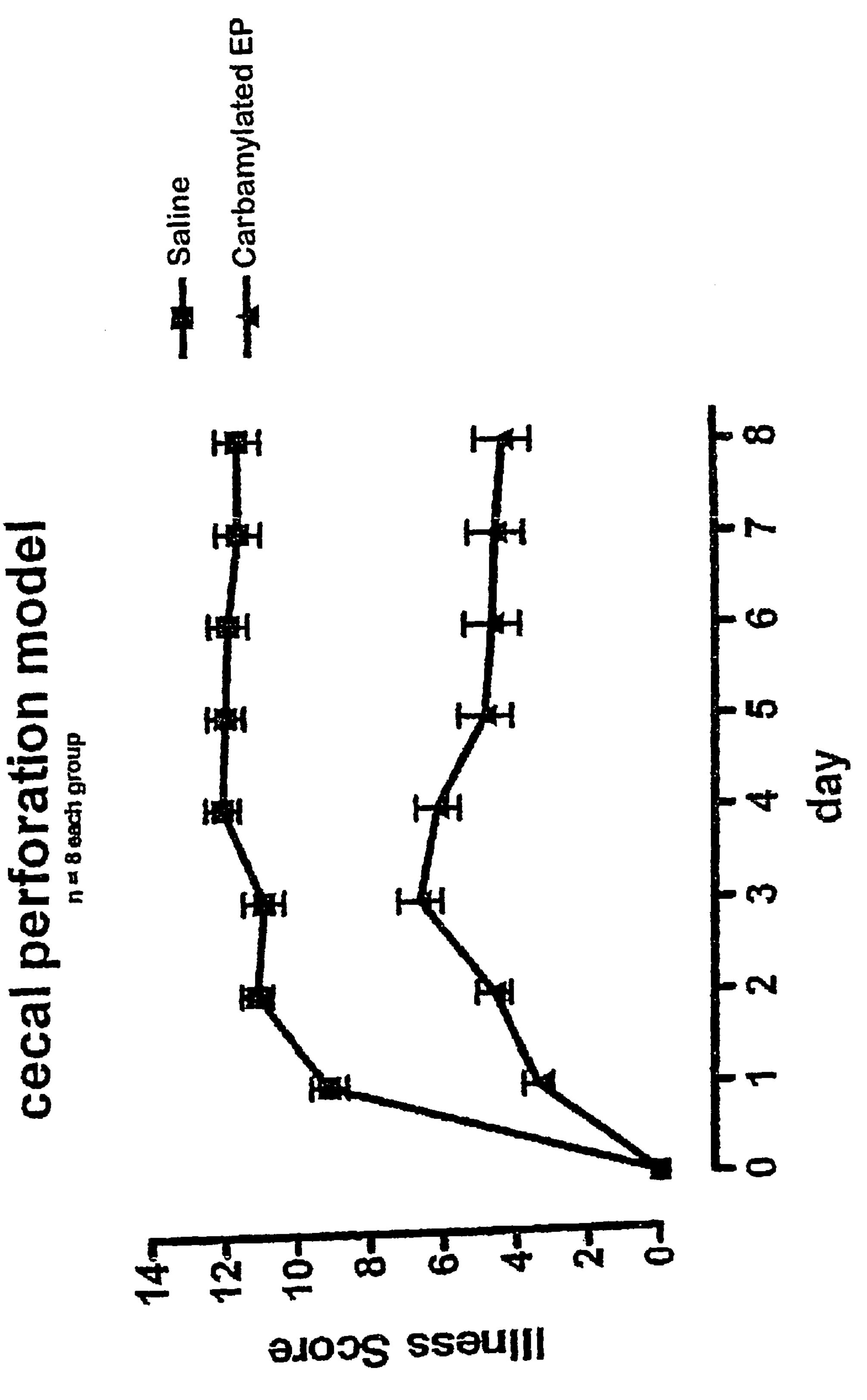
FIG. 3 is a graphical representation of the illness score for Sprague Dawley rats subjected to CLP and subsequent treatment with saline or a tissue protective cytokine of the invention.

An illness score was calculated as described earlier in the application in Table 2 and the results are illustrated graphically in FIG. 3. In particular, one day following the treatment, the average illness score of Group 1 animals was about 9 compared to an average illness score of Group 2 animals of about 3. After 5 days, the Group 1 animals had an average illness score of about 12, whereas the Group 2 animals had an average illness score of about 5 or less.

Scarring

The rats were also visually examined for scarring from the incisions. Group 2 rats had less scarring than Group 1 rats.

Example 2

Blind Study Using Rat Abdominal Sepsis Model

The cecum of Sprague Dawley rats was exposed, ligated just distally to the ileocecal valve to avoid intestinal obstruction, punctured twice with a 18-gauge needle, squeezed gently to force out a small amount of feces, and then returned to the abdominal cavity (feces introduced in peritoneum, which induced infection). The abdomen was closed with 3-0 silk sutures.

The animals were allocated to three groups:

Group 1: Opened as described above, but no sepsis induced (n=6).

Group 2: Sepsis induced, treated with saline (n=8). At time of ligation, animals in Group 2 were given 100 μl saline intraveneously. Daily subcutaneous saline administration (100 μl) followed for 8 days (or until death).

Group 3: Sepsis induced, treated with carbamylated EPO (n=8). At time of ligation, animals were given 10 μg/kg carbamylated EPO in 100 μl saline intraveneously. Daily subcutaneous treatment followed for 8 days (or until death) at a dosage amount of 10 μg/kg in 100 μl saline.

Cumulative Adhesion Score

Specimens were taken from the peritoneal fluid and abscesses for aerobic and anaerobic culture. For aerobic culture, samples were incubated on blood on EMB agar for 24 hours at 37° C. For anaerobic culture, samples were layered on anaerobic blood agar and incubated in a Gas-Pak jar for 24 hours at 37° C. Growing colonies were identified with standard bacteriologic techniques.

Figure 4:
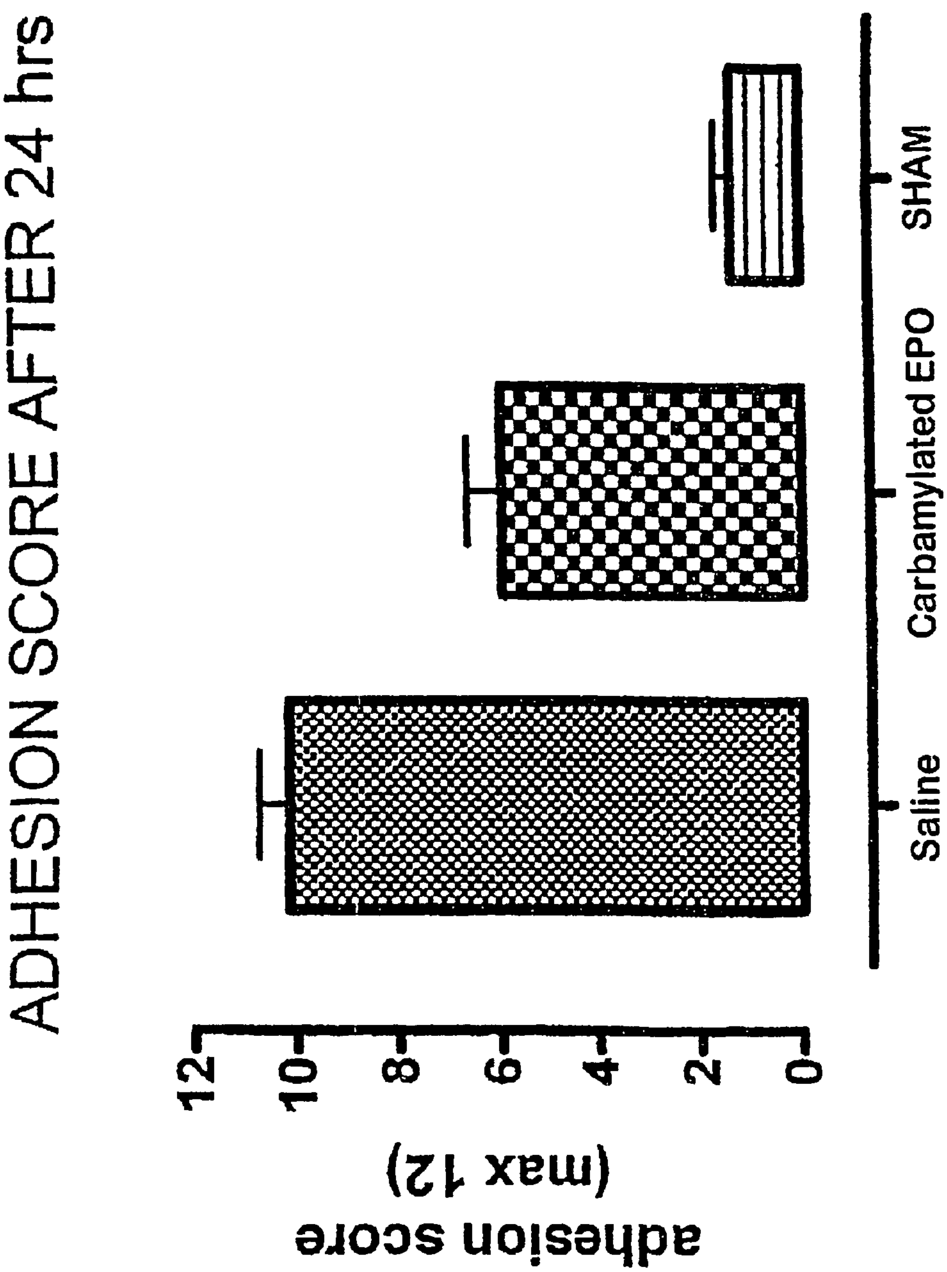
FIG. 4 is a graphical representation of the adhesion score for Sprague Dawley rats following CLP with and without sepsis introduction and subsequent treatment with saline and a tissue protective cytokine of the invention.

Dead animals were autopsied within 4 hours and the causes of death were recorded. Using Table 1 described earlier in the application, a cumulative adhesion score was calculated for each animal 24 hours post-injury and then averaged for the group (shown graphically in FIG. 4). In particular, the average total score of Groups 1, 2, and 3 were less than about 2, about 10 and about 6, respectively. Thus, the animals receiving the carbamylated EPO of the present invention had less adhesions than animals receiving saline.

Tumor Necrosis Factor Study

Figure 5:
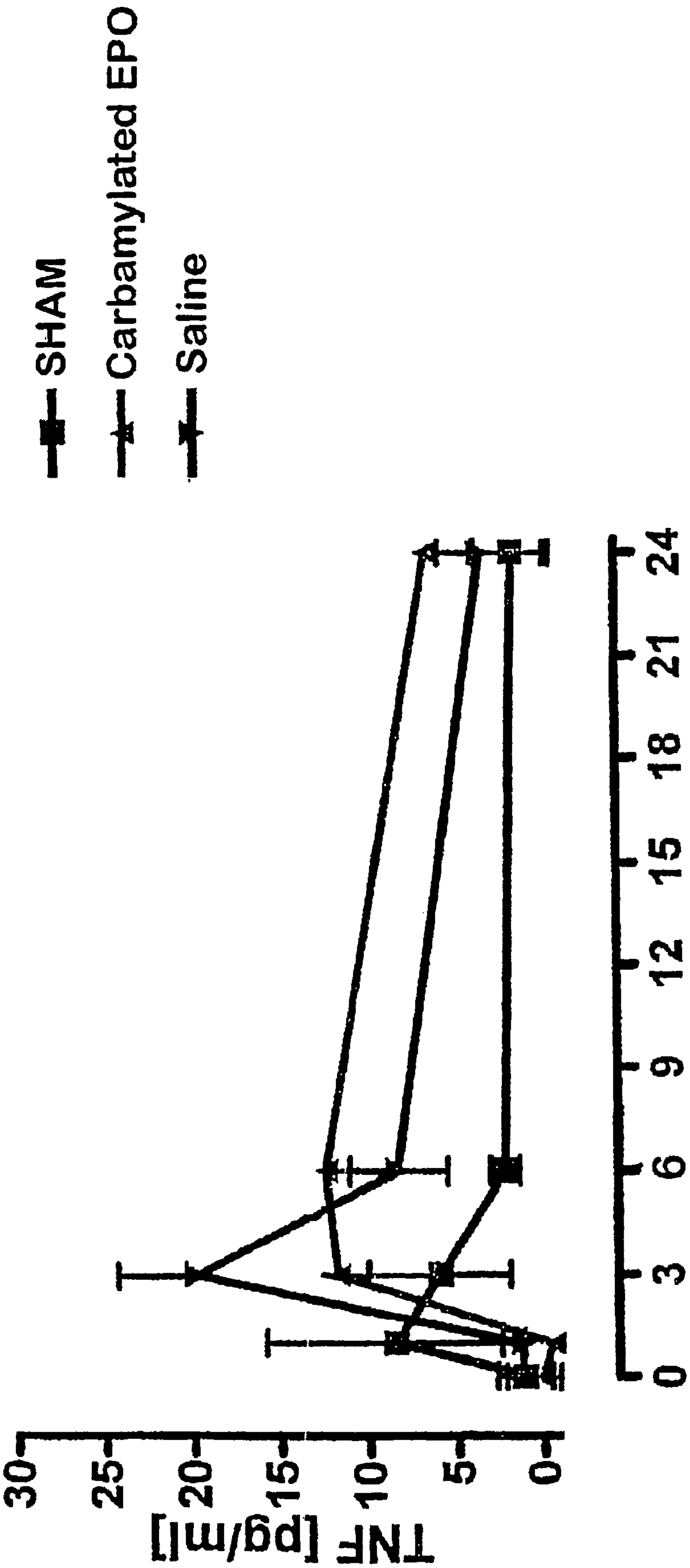
FIG. 5 is a graphical representation of the serum TNF level for Sprague Dawley rats following CLP with and without sepsis introduction and subsequent treatment with saline and a tissue protective cytokine of the invention.

The level of tumor necrosis factor (TNF) present in the blood of animals after a period of time was examined using an ELISA from R&D Systems (#RTA00) capable of to detecting rat TNF-alpha for each group in an effort to determine a mechanism behind carbamylated EPO's ability to decrease adhesions. As shown in FIG. 5, the difference in the amount of TNF after 24 hours is not significantly different between the three groups. After three hours (peak inflammation), the amount of TNF in the system decreased for all three groups. These results suggest that the accepted mechanism behind adhesions, i.e., an inflammatory response, may not be the accurate mechanism. In fact, the TNF study suggests that the mechanism behind adhesion may be due to cell death and, because the carbamylated EPO of the present invention has a tissue protective function, the adhesions may decrease upon administration because of decreased cell necrosis.

Scarring

Upon visual examination, the rats in Group 3 had substantially less scaring than Groups 1 and 2.

Example 3

Blind Study Using Abdominal Sepsis Model

The cecum of Sprague Dawley rats was exposed, ligated just distally to the ileocecal valve to avoid intestinal obstruction, punctured twice with a 18-gauge needle, squeezed gently to force out a small amount of feces, and then returned to the abdominal cavity (feces introduced in peritoneum, which induced infection). The abdomen was closed with 3-0 silk sutures.

The animals were allocated to four groups:

Group 1: Opened as described above, but no sepsis induced (n=6).

Group 2: Sepsis induced, treated with saline (n=8). At time of ligation, animals in Group 2 were given 100 μl saline intraveneously. Daily subcutaneous saline administration (100 μl) followed for 8 days (or until death).

Group 3: Sepsis induced, treated with rhu-EPO (n=8). At time of ligation, animals were given 10 μg/kg rhu-EPO intraveneously in 100 μl saline. Daily subcutaneous treatment followed for 8 days (or until death) at a dosage amount of 10 μg/kg in 100 μl of saline.

Group 4: Sepsis induced, treated with carbamylated EPO (n=8). At time of ligation, animals were given 10 μg/kg carbamylated EPO intraveneously in 100 μl saline. Daily subcutaneous treatment followed for 8 days (or until death) at a dosage amount of 10 μg/kg in 100 μl saline Morbidity and Mortality One day following ligation, all of the animals in Group 1 (sham) survived, whereas none of the animals in Group 2 survived. Only 2 of the animals in Group 3 (rhu-EPO) survived compared to 5 animals in Group 4. Thus, the animals receiving the carbamylated EPO of the present invention had a much higher survival rate than animals receiving saline or rhu-EPO.

Scarring

Upon visual examination, the rats in Group 4 had substantially less scarring than Groups 1-3.

Example 4

Lipopolysaccharide Induced Response in Rats

The purpose of this example was to determine the effectiveness of carbamylated erythropoietin on sepsis-like symptoms induced by lipopolysaccharide (LPS). LPS is an endotoxin present on the surface of bacteria which induces sepsis-like response (core temperature increase and cytokine induction) in animals. Male Sprague/Dawley rats (300-350g) were administered 240 ug/kg, i.p. The animals were then treated with saline (n=6) or carbamylated erythropoietin (n=6) at 10 ug/kg, i.v. The concentration dependent effects of LPS on core body temperature were then determined. Alternatively, the direct intraventricular application (Seeley et al, (1996) *Horm Metab Res.* 28:664-8.) of carbamylated erythropoietin (5 ug/kg in 2 ul) was administered to determine if the route of application alters the core temperature differentially. Core temperature will be monitored during the first 24 hrs. In some cases, blood was removed for subsequent cytokine (e.g., TNF, IL-6) analysis. Seeley et al, (1996) *Horm Metab Res.* 28:664-8.

Core Temperature.

As part of the sepsis-like conditions induced by LPS, the animals administered LPS experience a biphasic fever. The first phase of the fever is characterized by a precise increase in temperature accompanied by an increase in blood pressure and wakefulness of the afflicted individual. Whereas the second phase of the fever is less precise, and is accompanied by either normotension or hypotension as well as lethargy and sleepiness. It is theorized that the phases of the fever represent a transition in the strategy that the body utilizes to combat the sickness. (Romanovsky et al., *Am. J. Physiol,* 271: R244-R253, 1996) In the present example, the administration of carbamylated erythropoietin to LPS treated animals resulted in a reduction in both phases of the fever as demonstrated by FIG. 6.

Serum Levels of TNF and Il-6.

Carbamylated erythropoietin's ability to mediate the fever response to LPS was further correlated by its ability to suppress the presence of pyrogenic cytokines such as TNF and IL-6, as demonstrated in FIG. 7(*a*) and FIG. 7(*b*). ELISA was used to determine the presence of TNF and IL-6 within the serum sampled from the rats. Both FIGS. 7(*a*) and 7(*b*) demonstrate that the treatment with carbamylated erythropoietin significantly reduced the presence of pro-inflammatory cytokines, IL-6 and TNF.

Peripheral v. Central Administration of Carbamylated Erythropoietin.

Figure 8A:
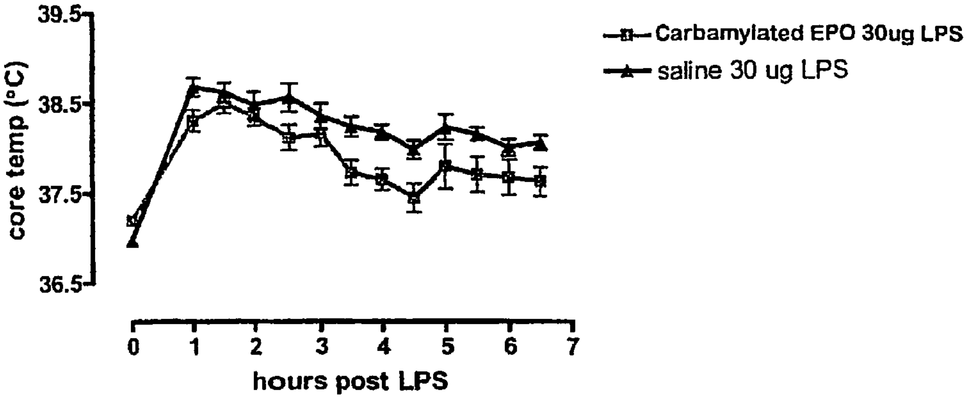
FIGS. 8(*a*) and (*b*) are charts demonstrating the core body temperature of Sprague Dawley rats treated with a tissue protective cytokine peripherally (FIG. 8*a*) or centrally (FIG. 8*b*) after LPS induced sepsis.
Figure 8B:
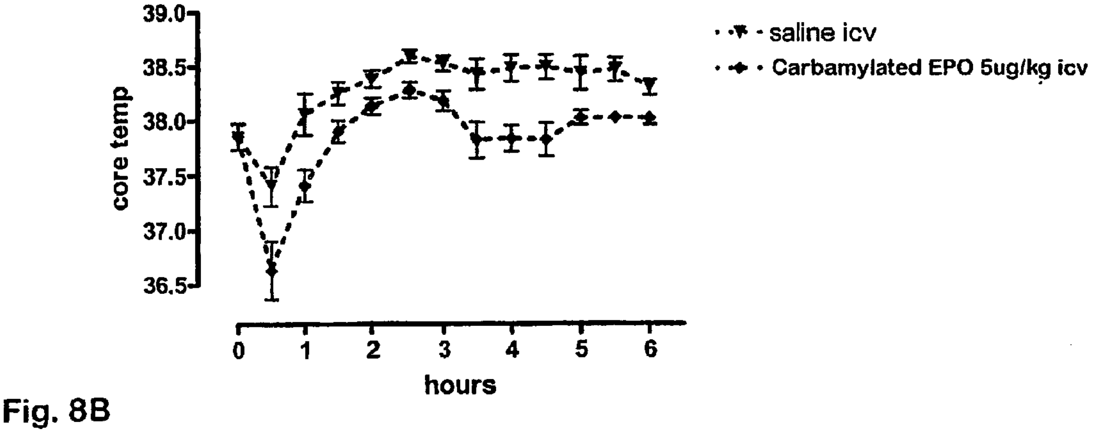

In order to rule out the direct effect of carbamylated erythropoietin upon the hypothalamus, the carbamylated erythropoietin was administered intraventricularly in the manner noted above. As FIG. 8(*a*) and FIG. 8(*b*) demonstrate, there was no correlation in the reduction of core temperature between the peripherally and centrally administered carbamylated erythropoietin. In light of these results as well as carbamylated erythropoietin's effects on the pyrogenic cytokines, it appears that carbamylated erythropoietin effects the core temperature through the suppression of the pyrogenic cytolines. This suggests that tissue protective cytokines, such as carbamylated erythropoietin, are useful in mediating, ameliorating or preventing the effects of these cytokines in chronic illnesses (wasting, lethargy, anemia, etc.).

Example 5

Effect of Erythropoietin analogues on Ischemic Skin Flap Iniury in Rats

Figure 9:
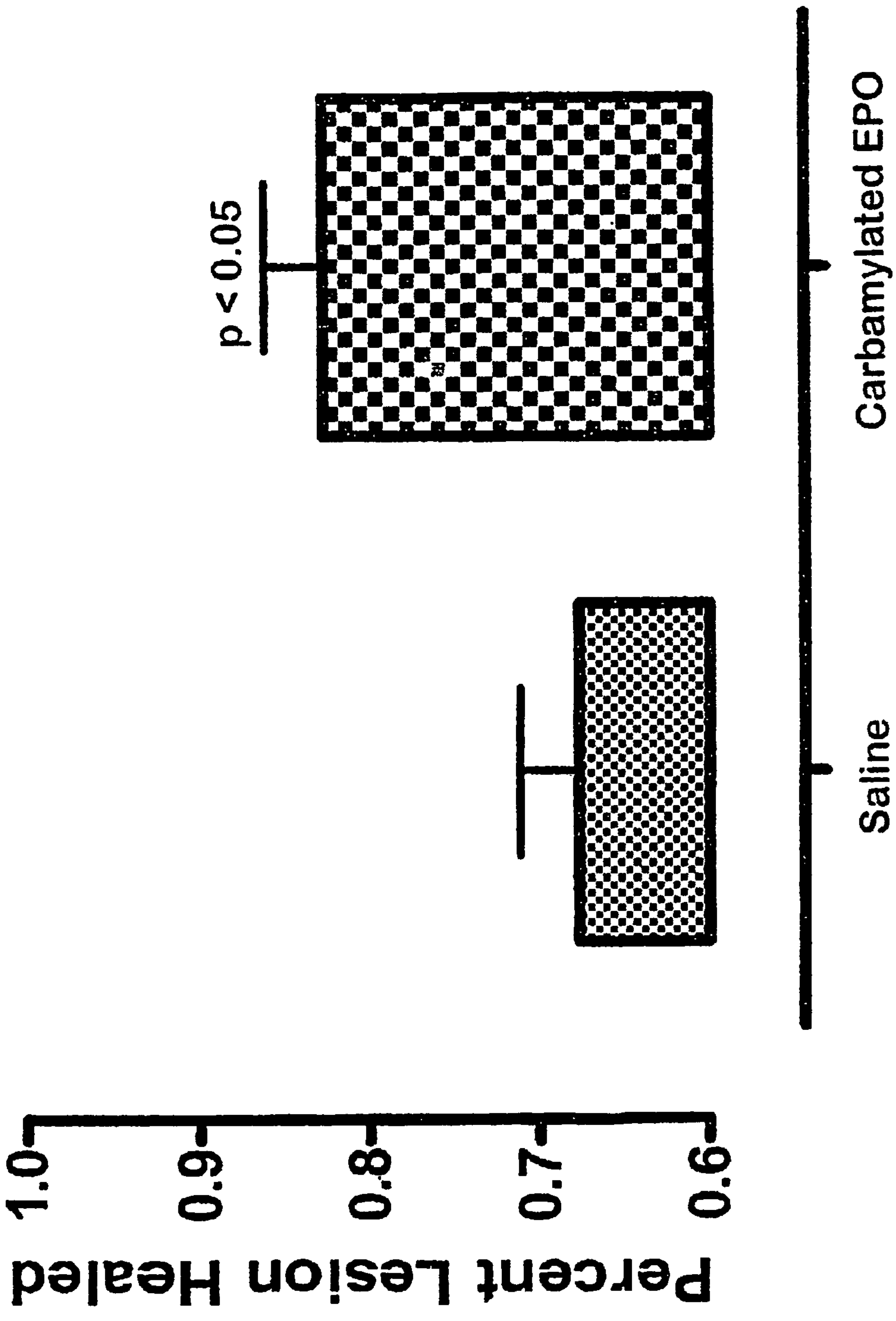
FIG. 9 is a graphic representation of the percentage of lesion healed in Sprague Dawley rats thirty-four (34) days after being subjected to an ischemic skin flap test and subsequently treated with saline or a tissue protective cytokine.

An ischemic wound flap model was performed to determine the effect of carbamylated erythropoietin on ischemic skin flap wound recovery. Male Sprague/Dawley rats (300-350 g) were anesthetized using isoflurane. A skin flap 9 cm long and 3 cm wide was then cut in the back of the rat. The flap included skin, subcutaneous layer and panniculus camosus. Following incision, the flap was raised and then immediately re-sutured in its bed, as described (Buemi, M., et al., (2002) *Acta Derm. Venereol.* 82:411-417; Sarau, A., et al., (2003) *Laryngoscope.* 113:85-89). Animals were dosed with an erythropoietin analogue, carbamylated EPO, (0.3 μg/kg, s.c.) immediately following surgery, day 1, day 2 and then bi-weekly during analysis. Animals were weighed and the wound photographed weekly. Buerni, M., et al., (2002) *Acta Derm. Venereol.* 82:411-417. The area of the wound healed was then quantified based on photographs of the animals taken 34 days following the proceedure. As is demonstrated in FIG. 9, the rats that received carbamylated erythropoietin had a greater percentage of the wound healed than those treated with saline for the same time period.

The invention described and claimed herein is not to be limited in scope by the specific embodiments herein disclosed, since these embodiments are intended as illustrations of several aspects of the invention. In particular, one of ordinary skill in the art will recognize that althought the above examples were performed using carbamylated EPO, similar results would be expected of any of the tissue protective cytokines of the present invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All patents and patent applications cited in the foregoing text are expressly incorporate herein by reference in their entirety.

What is claimed is:

1. A method of treating, delaying the onset of, or reducing adhesion formation, abnormal fibrous band formation, formation of a connection between organs, or scarring in a mammal comprising administering to the mammal a therapeutically effective amount of at least one erythropoietin that is chemically modified at one or more lysine residues or the N-terminal amino group, wherein said chemical modification is carbamylation, and a pharmaceutical carrier.

2. The method of claim 1, wherein said erythropoietin lacks or is diminished for at least one or more of erythropoietin's erythropoietic effects.

3. The method of claims 1, wherein the carbamylation of the erythropeietin on at least six lysine residues thereof, at least seven lysine residues thereof, or at least eight lysine residues thereof.

4. The method of claim 1, wherein the adhesion formation is a result of one or more of surgery, trauma, infection, chemotherapy, radiation, or cesarean section.

* * * * *

UNITED STATES PATENT AND TRADEMARK OFFICE

CERTIFICATE OF CORRECTION

PATENT NO. : 7,645,733 B2
APPLICATION NO. : 10/573905
DATED : January 12, 2010
INVENTOR(S) : Michael Brines et al.

It is certified that error appears in the above-identified patent and that said Letters Patent is hereby corrected as shown below:

On the title page, under item (73) Assignees, replace "The Kenneth S. Warren Institute, Inc., Ossining, NY (US); Warren Pharmaceuticals, Inc., Ossinin, NY (US)" with -- The Kenneth S. Warren Institute, Inc., Ossining, NY (US); Warren Pharmaceuticals, Inc., Ossining, NY (US) --.

Claim 3, at column 28, lines 25-28, replace "method of claims 1, wherein the carbamylation of the erythropeietin on at least six lysine" with -- method of claim 1, wherein the carbamylation of the erythropoietin is on at least six lysine --.

Signed and Sealed this

Fifteenth Day of June, 2010

David J. Kappos
*Director of the United States Patent and Trademark Office*

UNITED STATES PATENT AND TRADEMARK OFFICE

CERTIFICATE OF CORRECTION

PATENT NO. : 7,645,733 B2 
APPLICATION NO. : 10/573905
DATED : January 12, 2010
INVENTOR(S) : Brines et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 540 days.

Signed and Sealed this

Sixteenth Day of November, 2010

David J. Kappos
*Director of the United States Patent and Trademark Office*